US009388475B2

(12) United States Patent
Lee

(10) Patent No.: US 9,388,475 B2
(45) Date of Patent: Jul. 12, 2016

(54) METHOD OF AND SYSTEM FOR PRODUCING OIL AND VALUABLE BYPRODUCTS FROM GRAINS IN DRY MILLING SYSTEMS WITH A BACK-END DEWATER MILLING UNIT

(71) Applicant: Chie Ying Lee, Fremont, CA (US)

(72) Inventor: Chie Ying Lee, Fremont, CA (US)

(73) Assignee: Lee Tech LLC, Fremont, CA (US)

(*) Notice: Subject to any disclaimer, the term of this patent is extended or adjusted under 35 U.S.C. 154(b) by 439 days.

(21) Appl. No.: 13/971,768

(22) Filed: Aug. 20, 2013

(65) Prior Publication Data

US 2014/0053829 A1 Feb. 27, 2014

Related U.S. Application Data

(60) Provisional application No. 61/692,593, filed on Aug. 23, 2012, provisional application No. 61/822,053, filed on May 10, 2013.

(51) Int. Cl.

| C13K 13/00 | (2006.01) |
|---|---|
| A23K 1/06 | (2006.01) |
| B02C 9/04 | (2006.01) |
| C11B 13/00 | (2006.01) |
| C13K 1/02 | (2006.01) |
| C12P 7/20 | (2006.01) |
| C12P 7/02 | (2006.01) |

(52) U.S. Cl.
CPC .............. *C13K 13/007* (2013.01); *A23K 1/06* (2013.01); *A23K 10/38* (2016.05); *B02C 9/04* (2013.01); *C11B 13/00* (2013.01); *C13K 1/02* (2013.01); *C12P 7/02* (2013.01); *C12P 7/20* (2013.01); *Y02P 60/873* (2015.11); *Y02W 30/74* (2015.05)

(58) Field of Classification Search
None
See application file for complete search history.

(56) References Cited

U.S. PATENT DOCUMENTS

| 2,600,903 | A |   | 6/1952 | Miller |
|---|---|---|---|---|
| 3,786,078 | A | * | 1/1974 | Smith et al. ............... C11B 1/04 554/15 |
| 3,827,423 | A |   | 8/1974 | Bolitho |
| 3,975,546 | A |   | 8/1976 | Stahmann |
| 4,042,172 | A |   | 8/1977 | Norzdrovsky |
| 4,171,383 | A |   | 10/1979 | Chwalek et al. |
| 4,255,518 | A |   | 3/1981 | Muller et al. |

(Continued)

FOREIGN PATENT DOCUMENTS

| DE | 4239342 A1 | 5/1994 |
|---|---|---|
| EP | 0772978 B1 | 11/1999 |

(Continued)

OTHER PUBLICATIONS

International Search Report and Written Opinion from PCT Application No. PCT/US15/47577.

*Primary Examiner* — Melvin C Mayes
*Assistant Examiner* — Stefanie Cohen
(74) *Attorney, Agent, or Firm* — Haverstock & Owens LLP

(57) ABSTRACT

A method of and system for producing oil and valuable byproducts from grains, such as corn, in dry mills are disclosed. The method and system include dewater milling process after fermenting. Further, the method and system are able to produce oil without evaporating. Moreover, the method and system include one or more of the germ processing units, emulsion processing units, fiber processing units, high value protein producing units, and glycerol and inorganic salt producing units, such that high value byproducts are able to be generated.

14 Claims, 17 Drawing Sheets

(56) References Cited

U.S. PATENT DOCUMENTS

| | | |
|---|---|---|
| 4,313,061 A | 1/1982 | Thomas |
| 4,341,713 A | 7/1982 | Stolp et al. |
| 4,396,161 A | 8/1983 | Ruokolainen et al. |
| 4,635,864 A | 1/1987 | Peterson et al. |
| 5,177,008 A | 1/1993 | Kampen |
| 5,244,159 A | 9/1993 | Newman |
| 5,248,099 A | 9/1993 | Lahner et al. |
| 5,364,335 A | 11/1994 | Franzen et al. |
| 6,190,462 B1 | 2/2001 | Markland et al. |
| 6,254,914 B1 | 7/2001 | Singh et al. |
| 6,899,910 B2 | 5/2005 | Johnston et al. |
| 7,563,469 B1 | 7/2009 | Navarro et al. |
| 2002/0122944 A1 | 9/2002 | Ogle et al. |
| 2004/0087808 A1 | 5/2004 | Prevost et al. |
| 2004/0187863 A1 | 9/2004 | Langhauser |
| 2005/0009133 A1 | 1/2005 | Johnston et al. |
| 2007/0184541 A1 | 8/2007 | Karl et al. |
| 2007/0210007 A1 | 9/2007 | Scheimann et al. |
| 2009/0093027 A1 | 4/2009 | Balan et al. |
| 2009/0227004 A1 | 9/2009 | Dale |
| 2010/0093860 A1 | 4/2010 | Boon et al. |
| 2010/0159552 A1 | 6/2010 | Benson et al. |
| 2010/0260918 A1* | 10/2010 | Wang ............ A23D 9/02 426/601 |
| 2011/0086149 A1 | 4/2011 | Bootsma |
| 2011/0100359 A1 | 5/2011 | North |
| 2011/0123657 A1 | 5/2011 | Vandenbroucke et al. |
| 2011/0177560 A1 | 7/2011 | Galvez, III et al. |
| 2011/0250312 A1 | 10/2011 | Lewis |
| 2011/0283602 A1 | 11/2011 | Gallop et al. |
| 2012/0077232 A1 | 3/2012 | Budaraju et al. |
| 2012/0168387 A1 | 7/2012 | Tran et al. |
| 2012/0199531 A1 | 8/2012 | Winsness |
| 2012/0244590 A1 | 9/2012 | Lee |
| 2012/0252065 A1 | 10/2012 | Rozenszain et al. |
| 2012/0270275 A1 | 10/2012 | Fenton et al. |
| 2014/0242251 A1 | 8/2014 | Bootsma |

FOREIGN PATENT DOCUMENTS

| | | |
|---|---|---|
| GB | 852995 A | 11/1960 |
| WO | 01/14595 A2 | 3/2001 |
| WO | 2012/075481 A1 | 6/2012 |
| WO | 2012145230 A1 | 10/2012 |
| WO | 2012160191 A2 | 11/2012 |

* cited by examiner

METHOD OF AND SYSTEM FOR PRODUCING OIL AND VALUABLE BYPRODUCTS FROM GRAINS IN DRY MILLING SYSTEMS WITH A BACK-END DEWATER MILLING UNIT

CROSS REFERENCE TO RELATED APPLICATION(S)

This application claims priority from U.S. Provisional Patent Application Ser. No. 61/692,593, filed Aug. 23, 2012 and entitled "A SYSTEM FOR AND METHOD OF SEPARATING OIL AND PROTEIN FROM GRAINS USED FOR ALCOHOL PRODUCTION" and U.S. Provisional Patent Application Ser. No. 61/822,053, filed May 10, 2013 and entitled "A SYSTEM FOR AND METHOD OF SEPARATING OIL AND PROTEIN FROM GRAINS USED FOR ALCOHOL PRODUCTION," which are hereby incorporated herein by reference in their entirety for all purposes.

FIELD OF THE INVENTION

The present invention relates to methods of and devices for a dry milling alcohol production system. More specifically, the present invention relates to methods of and systems for increasing the alcohol, byproduct oil, and protein yields for dry grinding ethanol plants.

BACKGROUND OF THE INVENTION

FIG. 1 is a typical wet milling process for alcohol production. FIG. 2 is a typical dry milling process with a back-end oil recovery system. FIG. 3 is a typical dry milling process with a back-end oil and protein recovery system.

Conventional methods of producing alcohols from grains generally use two procedures. One of the procedures is operated in a wet condition and the other is operated under a dry condition, which are referred to as a wet milling process and a dry milling process respectively. The wet milling corn processing plants convert corn grains into several different co-products, such as germs (for oil extraction), gluten feed (high fiber animal feed), gluten meal (high protein animal feed), and starch-based products (such as ethanol, high fructose corn syrup, and food) and industrial starch. The dry grind ethanol plants convert corns into two products including ethanol and distiller's grains with soluble. The distiller's wet grains with soluble is referred to as DWGS if it is sold as wet animal feed. The distiller's dried grains with soluble is referred to as DDGS if is dried to be used as an animal feed.

In the typical dry grinding mill process for ethanol production, one bushel of corn yields approximately 8.2 kg (approximately 17 lbs.) of DDGS in addition to an approximately 10.3 liters (approximately 2.75 gal) of ethanol. These co-products provide a critical secondary revenue stream that offsets a portion of the overall ethanol production costs. DDGS is typically sold as a low value animal feed even though that the DDGS contains 11% oil and 33% protein. Some plant starts to modify the typical processes by separating the valuable oil and protein from the DDGS.

It is reported that there are about 40 plants using a back-end oil recovery system, one plant having a protein recovery system, and one plant having a front grind milling with a front oil recovery system. These improved processes have the same goal that is to increase an alcohol yield of the plants as well as to recover valuable oil from the front-end process. Generally, a front-end process refers to steps and/or procedures that are performed before fermenting and a back-end process refers to steps and/or procedures that are performed after the fermenting.

In the following, some typical wet milling processes are disclosed. FIG. 1 is a flow diagram of a typical wet milling ethanol production process 10. The process 10 begins with steeping 11, in which corns (corn kernels that contain mainly starch, fiber, protein, and oil) are soaked for 24 to 48 hours in a solution of water and sulfur dioxide to soften the kernels for grinding. In the steeping 11, soluble components leach into the steep water and the protein matrix and the endosperm are loosened. Next, the steeped corn (after the steeping 11) with about 50% of DS is fed to a determination milling 12 (first grinding) at a grinding mill, in which the corn is ground in a manner that tears open the kernels and releases the germ so as to make a heavy density (8 to 9.5 Be) slurry of the ground components, which is primarily a starch slurry.

Next, germ separating 13 is performed by floating germs and a hydrocyclone(s) is used to separate the germ from the rest of the slurry. The germs contain oil, which are inside the kernel. The separated germs in a stream (separated out as a germ byproduct) contain some portions of starch, protein, and fiber. The separated germs are sent to a germ washing 13A, such that the starch and protein are able to be removed. Next, the germ stream is sent to a dryer. About 2.5 to 3 lbs. (dry basis) of germs per bushel of corn are generated. The dry germs have about 50% of oil content on a dry basis.

The remaining slurry from the germ separating 13, which is now devoid of germs containing fiber, gluten (e.g., protein), and starch, is subjected to fine grinding 14 (second grinding) at a fine grinding mill, where total disruption of endosperm occurs. The endosperm components are released (including gluten and starch) from the fiber.

Next, fiber separating 15 is performed. In the fiber separating 15, the slurry passes through a series of screens to separate the fibers from the starch and gluten. The fibers are washed to be clean of the gluten and starch. The fiber separating 15 typically employs static pressure screens or rotating paddles mounted in a cylindrical screen (paddle screens). Even after washing, the fibers from a typical wet grinding mill still contain 15%~20% of starch. This starch is able to be sold with the fibers as animal feed. The remaining slurry, which is now devoid of fiber, is subjected to gluten separating 16, in which the centrifugations separate starch from the gluten. The gluten stream (at gluten filtrating and drying 16A) goes to a vacuum filter followed by a drying step at a dryer to produce gluten (protein) meal.

Next, liquefying/saccharifying 17, fermenting 18, distilling/dehydrating 19 are performed. At the liquefying/saccharifying 17, the starch from the starch gluten separating 16 goes through a jet cooker to start the process that converts the starch to sugar. Jet cooking refers to a cooking process that is performed at elevated temperatures and pressures. The elevated temperatures and pressures are able to be varied widely. Typically, jet cooking occurs at a temperature about 120° C. to 150° C. (about 248° F. to 302° F.) and a pressure about 8.4 kg/cm$^2$ to 10.5 kg/cm$^2$ (about 120 lbs./in$^2$ to 150 lbs./in$^2$), although the temperature is able to be as low as about 104° C. to 107° C. (about 220° F. to 225° F.) when a pressure of about 8.4 kg/cm$^2$ (about 120 lbs./in$^2$) is used. Liquefying occurs when the mixture or "mash" is held at 90° C. to 95° C. Under such condition, alpha-amylase hydrolyzes the gelatinized starch into maltodextrins and oligosaccharides (chains of glucose sugar molecules) to produce a liquefied mash or slurry. The process of saccharifying is performed by cooling the liquefied mash to about 50° C. and adding a commercial available enzyme known as gluco-amylase. The gluco-amylase hydrolyzes the maltodextrins and short-chained oligosaccharides into single glucose sugar molecules to produce a liquefied mash.

In fermenting 18, a common strain of yeast (Saccharomyces crevasse) is added to metabolize the glucose sugars into ethanol and $CO_2$. Upon completion, the fermented mash ("beer") contains about 17% to 18% ethanol (volume/volume basis). Subsequent to the fermenting 18 is the distilling and dehydrating 19, in which the beer is pumped into distillation columns where it is boiled to vaporize the ethanol. The ethanol vapor is condensed in the distillation columns, and liquid alcohol (e.g., ethanol) exits the top of the distillation columns at about 95% purity (190 proof). Next, the 190 proof of ethanol goes through a molecular sieve dehydration column, which removes the remaining residual water from the ethanol, such that a final product of essentially 100% of ethanol (199.5 proof) is produced. This anhydrous ethanol is now ready to be used for motor fuel purposes. The solids and some liquid remaining after distilling go to evaporating 20, where yeast is able to be recovered as a byproduct. Yeast is able to be optionally recycled back to the fermenting 18. In some embodiments, the $CO_2$ is recovered and sold as a commodity product. The "stillage" produced after distilling and dehydrating 19 in the wet milling process 10 is generally called "syrup."

The wet grinding process 10 is able to produce a high quality starch product that is able to be converted to alcohol, as well as separate streams of germs, fiber and protein, which are able to be sold as byproducts to generate additional revenue streams. However, the wet grinding process is complicated and costly requiring high capital investments as well as high-energy costs for operation.

Because the capital costs of wet grinding mills are so prohibitive, some alcohol plants prefer to use a simpler dry grinding process. FIG. 2 is a flow diagram of a typical dry grinding ethanol production process 20. As a general reference point, the dry grinding ethanol process 20 is able to be divided into a front-end and a back-end process. The part of the process 20 that occurs prior to fermenting 23 is considered the "front-end" process, and the part of the process 20 that occurs after fermenting 23 is considered the "back-end" process.

The front-end process of the process 20 begins with grinding 21, in which dried whole corn kernels are passed through hammer mills to be ground into corn meal or a fine powder. The screen openings in the hammer mills are typically of a size 7, or about 2.78 mm, with the resulting particle distribution yielding a very wide spread and bell type curve particle size distribution, which includes particle sizes as small as 45 micron and as large as 2 to 3 mm. The ground meal is mixed with water to create slurry and a commercial enzyme called alpha-amylase is added (not shown). This slurry is then heated to approximately 120° C. for about 0.5 to three (3) minutes in a pressurized jet cooking process in order to gelatinize (solubilize) the starch in the ground meal. It is noted that in some processes a jet cooker is not used and a longer hold time is used instead.

The grinding 21 is followed by liquefying 22, whereat the ground meal is mixed with cook water to create slurry and a commercial enzyme called alpha-amylase is typically added. The pH is adjusted here to about 5.8 to 6 and the temperature is maintained between 50° C. to 105° C., so as to convert the insoluble starch in the slurry to become a soluble starch. The stream after the liquefying 22 has a content of about 30% of dry solids (DS) with all the components contained in the corn kernels, including sugars, protein, fiber, starch, germ, grit, and oil and salt. There are generally three types of solids (fiber, germ, and grit) with similar particle size distribution in the liquefying stream.

The liquefying 22 is followed by a simultaneous saccharifying and fermenting 23. This simultaneous process is referred to in the industry as "Simultaneous Saccharification and Fermentation" (SSF). In some commercial dry grinding ethanol processes, saccharifying and fermenting occur separately (not shown). Each of the individual saccharifying and SSF is able to take as long as about 50 to 60 hours. In the fermenting 23, sugar is converted to alcohol using a fermenter. Next, distilling and dehydrating 24 are performed, which utilizes a still to recover the alcohol.

In the back-end process of the process 20, which follows distilling and dehydrating 24, preconcentrating 28, fiber separating 25 (centrifuging the "whole stillage" produced at the distilling and dehydrating 24, such that the insoluble solids ("wet cake") is able to be separated from the liquid ("thin stillage")), and evaporating 27.

The "wet cake" from the distilling and dehydrating 24 includes fiber (per cap, tip cap, and fine fiber), grit, germ particle and some protein. The liquid from the centrifuge contains about 6% to 8% of DS, which contains mainly oil, germ, fine fiber, fine grit, protein, soluble solid from the fermenter and ash from corns. The whole stillage at some plant having about 12 to 14% of DS, which is fed to preconcentrating 28 of a first stage evaporator to concentrate the whole stillage to 15 to 25% of DS before feeding the whole stillage to the fiber separation step 25.

At the fiber separating 25, a decanter centrifuge is used to split the whole stillage into two streams (a cake stream and a liquid stream). The cake stream contains mainly fiber and sine protein, grit and germ particle. The liquid stream, which is commonly called a thin stillage, contains insoluble solid (such as protein, germ and fine fiber) and soluble solid from corn. Next, the thin stillage is split into two streams. One stream includes about 30%—40% of flow is recycled back (as a "back-set" stream) to be mixed with corn flour in a slurry tank at the beginning of the liquefying 22. The other stream containing the rest of the flow (about 60 to 70% of the total flow) enters evaporators in evaporating 27 to boil away moisture leaving a thick syrup that contains mainly fine solid (protein, germ and fine fiber) and soluble (dissolved) solids from the fermenting (25% to 40% dry solids).

The back-set water is used as part of cooking water in the liquefying 22 to reduce the fresh water consumption as well as save evaporating energy and equipment costs.

The concentrated slurry from the evaporating 27 is able to be subjected to back-end oil recovering 26, where the slurry is able to be centrifuged to separate oil from the syrup. The oil recovered is able to be sold as a separate high value product. The oil yield is normally about 0.4 lbs./Bu of corn with a high free fatty acid content. This oil yield only accounts for about ¼ of the oil in the corn. About one-half of the oil of the corn kernel remains inside the germ after the distilling 24, which cannot be separated in a typical dry grind process that uses centrifuges. The free fatty acids, which are created when the oil is held in the fermenter for approximately 50 hours, reduce the value of the oil.

The (de-oil) centrifuges is able to remove only less than 50% oil in the syrup because the protein and oil make an emulsion, which cannot be satisfactorily separated. Although adding chemicals, such as emulsion breaker, is able to improve the separation efficiency in some degrees, the chemicals are costly and the DDGS product is able to be contaminated by the added chemicals. In some cases, heat is provided or the feed temperature is raised at the centrifuge to break the emulsion, but the method affects the color and quality of DDGS. In some other cases, alcohol is added to break the emulsion, which is also able to improve the separation and increases the oil yield. However, alcohol adding needs exploration proof equipment's and costly operations. All those improvements only increase the oil yield from an average of 0.4 lbs./Bu to about average 0.6 lbs./Bu even though the "free" oil (extractable oil) in the whole stillage is about 1 lbs./Bu. The main reason for having such a low oil yield in the back-end of the typical method is that the oil and protein form emulsion during the whole dry mill process, which makes the oil recovery difficult.

An oil and protein recovery process is developed by oil/protein separating that is added to break this oil/protein emulsion of a whole stillage. As shown in the process 30 of FIG. 3, the front-end process is similar to the typical dry mill process. The process changes its procedures after the fiber separating 25 in the back-end process. This oil/protein separating 31 is able to be added between the fiber separating 25 and evaporating 27. The nozzle centrifuges, other types of disc centrifuges, or decanters are normally used for this case.

The thin stillage from the fiber separating 25 is fed to oil/protein separating 31. The oil/protein emulsion is broken up in a higher G force inside the centrifuge. The oil is in a light phase (overflow) discharge and protein is in a heavy phase discharge (underflow), because of the density difference between oil (density 0.9 gram/ml) and protein (1.2 gram/ml).

The light phase (overflow) of the oil/protein separating 31 is fed to evaporating 27 to be concentrated to contain 25%~40% of DS (forming a semi-concentrated syrup). Next, the semi-concentrated syrup is sent to back-end oil recovering 26 to recover oil in the back-end process. The light phase stream contains less protein, so it has less chance to form oil/protein emulsion. The oil yield with this system is able to be as high as 1 lb./Bu. The de-oil syrup from the back-end oil recovering 26 is able to be further concentrated in an evaporator to a much higher syrup concentration as high as 60% of DS. The de-oil syrup with low protein is able to avoid fouling at the evaporator.

The underflow from oil/protein separating 31 is sent to a protein dewatering 32, such that the protein is able to be recovered. The separated protein cake from the protein dewatering 32, with a content having less than 3% of oil, is sent to protein drying 33 at a protein dryer to produce high value protein meal, which has a 50% of protein. The liquid from the protein dewatering 32 is sent back to the front-end as a backset stream that is used as part of cooking water in the liquefying 22.

All of the oil that is recovered from the back-end oil recovering system has poor quality, dark color, and high fatty acid around (15 to 20%), because the oil is in the fermenter more than 50 hours. The back-end oil separation is also able to be difficult to be carried out, because the oil and protein form emulsion during the whole dry milling process. Each step in the whole dry milling process, such as pump and separation create some oil/protein emulsion. In order to get good quality oil and avoid the formation of the oil/protein emulsion during whole dry milling process, recovering oil in the front-end is able to be a good solution.

The three phases decanter that are used to recover the oil from the liquefied starch stream at the liquefying are tested, but because the high viscosity in the liquefied starch solution plus most oil still in a germ form, the oil yield is normally low at around 0.2 lbs./Bu. Nonetheless, the oil quality is much better than oil obtained from the back end having a much lighter color with about 5 to 9% of free fatty acid.

SUMMARY OF THE INVENTION

An improved front-end oil recovery system are developed to improve the oil yield as well as to increase yield of the alcohol. As shown in the process 40 of FIG. 4, the two stages liquid/solid separating 42 and 44 are followed by two stage dewater milling 43 and 45 in series respectively with counter current setup, in which a portion of the cook water is added to holding tank 46 (such as from solid/liquid separating 49) instead of adding to the slurry tank 41.

In the process 40, the cook water (from fiber separating 25) is mixed with a cake from the second dewater milling 45 to form a mixture. The mixture is fed to a third solid/liquid separating 49 to recover liquid which is about 7 to 10 degree of Brix. The liquid from solid/liquid separating 49 is mixed with the cake from the first dewater milling 43 to the holding tank 46 for about 4 to 6 hours. The content in the holding tank 46 is fed to second solid liquid separating 44 to separate the liquid from the solid. The liquid separated at second solid liquid separating 44 has about 15 to 20 Brix, which is used as part of cook water to be mixed with corn flour from the hammer milling 21, to be sent to the slurry tank 41 with jet cooking. Using this counter current washing setup, the germ particle has about double the holding time in the holding tank 46 resulted in a much lower Brix (around 7 to 10 Brix instead of 25 to 30 Brix) liquefied starch solution. The germ that is soaked in a lower Brix environment and has double holding time in the liquefying is able to be softened more easily, such that the germ is able to be broken up and to release the oil at the second dewater milling 45. This counter current washing setup 44A in the process 40 also gives middle size germ particles from the second dewater milling 45, which is recycled back to the first dewater milling 43 to ensure that the germ particles are milled to become a predefined size of the germ particles (such as smaller than 150 micron) to release more oil. Further, all of the grit/germ/fiber solid particles have a wide range of particle size range from less than 45 micron to as large 2 to 3 mm. With softening the germ particle in a lower Brix solution with a longer holding tank time, the germ is much softer and easy to be broken up than the fibers. Accordingly, the dewatered milling process is able to break up more germ particles than fiber. However, each dewatered milling is able to only reduce the germ particle size about half of its original size at best. For example, the germ particle of an average size of 1,000 micron becomes about 600 micron in average after one pass of dewatered milling. For germ particles to release oil, the germ particle size is preferred to be less than 150 micron. Therefore, normally at least two/three stages dewatered millings in series are needed to release more oil from the germ particles.

The counter current washing setup 44A allows middle size germs after the second dewater milling 44 to be recycled back to the first dewater milling 42 for breaking the germ particles one more time. The screen size openings on the first and second solid/liquid separating 42 and 44 are selected to give a predetermined degree of sizes, such that the germ particles are able to be recycled back to the slurry tank.

After the slurry tank 41, the mixture is sent to the jet cooking, the second slurry tank, or one or more holding tanks. Next, the slurry is sent to the first solid/liquid separating 42, such that the liquid is separated from the solid.

At solid/liquid separating 42, the liquid that contains oil and small solid particle (germ, protein, and fine fiber) in liquefied starch solution is sent to front-end oil recovering systems including oil separating 47 and oil purifying 48. The de-water solid (cake) stream at the solid/liquid separating 42, containing mostly grit/germ/fiber, is sent to the first dewater milling 43 to break the solid particles (germ/grit/fiber), such that the starch and oil from grit/germ solid particles are released. Next, the solid from dewater milling 43 is mixed with the liquid from the third solid/liquid separating 49 to be sent to the holding tank 46. The back-set only has less than half of the whole cook water, so the solid (germ/grit/fiber) is able to stay in the holding tank more than double of a typical holding time and at much lower Brix. The grit/germ solid particles are able to be quickly and easily soften/broken up for the starch to be liquefied and for the oil to be released from the germ particles. After the holding tank 46, the slurry is sent to the second solid/liquid separating 44 to dewater/remove water. The liquid from the solid/liquid separating 44 is recycled back to the slurry tank 41 with larger germ particles as part of cook water. The cake from the second solid/liquid separating 44 is sent to the second dewater milling 45. Next, the cake from the second dewater milling 45 is mixed with back-set water from the protein separating 25 to the third solid/liquid separating 49. The liquid from the third solid/liquid separating 49 is sent to the holding tank 46. The cake from the solid liquid separating 49 is sent to the fermenter for fermenting 23.

The liquid from the first solid/liquid separating 42 that contains most of oil in the front-end is sent to a front-end oil recovering system including the oil separating 47 and the oil purifying 48. In oil separating 47, the three phase nozzle centrifuge is able to be used to separate the oil/emulsion/small germ particle from the liquefied starch solution. The light phase of the three phase nozzle centrifuge (containing most oil/emulsion/germ particles with small amount of liquefied starch solution) is sent to a small three phase separation centrifuge (decanter or disc centrifuge) to polish and purify oil in oil purifying 48. The heavy phase and underflow/cake phase from both a three phase nozzle centrifuge of oil separating 47 and a three phase separation centrifuge of oil purifying 48 are sent to fermenting 23 to be first converted to a sugar and then to an alcohol.

The "beer" from the fermenting that contains about 15%~17% of alcohol goes to distilling 24 for alcohol recovery. The whole stillage from the bottom of distilling 24 is able to be sent to the first stage evaporator for preconcentrating 46A from a normal 12%~14% DS to 15%~25% DS concentration. Next, germs in the germ removing 46B are separated by using a germ cyclone to float any larger germs that are still in the whole stillage. The use of the germ cyclone is able to increase the oil yield about 0.2 lb./Bu depending on the front grinding system and the concentration of the concentrated whole stillage and germ cyclone operation of the germ removing 46B. The de-germ fiber stream discharged from the bottom of the germ cyclone or the whole stillage discharged from the bottom of the distiller are sent to a decanter centrifuge at the fiber separating 25 to recover the fibers as DDG. The de-fiber stream from the decanter of the fiber separating 25 is split into two streams. One of the streams containing 30%~40% of the flow is used as a back-set stream/water. The other stream that is the remaining 60%~70% of the flow is sent to evaporating 27 to be concentrated to about 45% of DS as a syrup byproduct.

The oil recovery at a front-end system gives a lighter color and lower fatty acid (about 5 to 9%) oil. The oil yield at the front-end is affected by the numbers of dewater milling in the front-end and the numbers of the de-germ system in the back-end. With one dewater milling system, the oil yield is about 0.8~1 lbs./Bu. With two dewater milling in series, the oil yield is about 0.9 to 1.1 lbs./Bu. With an additional de-germ system in the back-end, the oil yield is about 1 to 1.2 lbs./Bu. Not all of the oil is able to be obtained in the front-end oil recovery system, because the oil in germ particles is only able to be released less than half of the oil in the front-end process.

The process 40A of FIG. 4A illustrate a dry milling process with front grinding mill and front end oil recovering system for oil production in accordance with some embodiments of the present invention. The process 40A includes dewater milling 45 and solid/liquid separating 49 in the back-end process to break the germ particles that fully absorb water such that more oil is able to be released. The dewater milling 45 and solid/liquid separating 49 are referred to as "Back-end germ particle breaking process."

The germ particles in the liquefaction stage do not fully absorb water and are not easy to be broken in dewater milling. Since the germ particle size normal decrease to half after dewater milling, more than half of oil inside the corn kernel is still trapped inside the germ (oil drop protect by protein cell wall) and do not release out with front dewater milling.

The germ particle after fermenting 23 and distilling 24 completely absorb water and become easy to break by grinding mill. Accordingly, the process 40A includes dewater milling 45 and solid/liquid separating 49 in the back-end (after fermenting 23) to break the germ particle, so that more oil is able to be released.

Further, more oil is able to be released from the germ particles at the back-end process by having an alcohol presented at the back-end, which acts as a solvent to extract more oil out during the fermenting 23, distilling 24, or even in the evaporating 27. In some cases, more than half (60%~70%) of the de-fiber stream is sent to the evaporating 27, so that the oil in this stream is not able to be recovered in the front-end. In some embodiments, an additional back-end oil recovery system 26 is used to have a higher oil yield. In addition, if the corns that are used are old or are dried in a high temperature environment, the germ particle softening process becomes very slow during the holding tank softening process. Accordingly in some embodiments, more enzymes and larger holding tank (to give longer holding time to soften germ) are used.

The methods of and devices for corn oil recovery in accordance with some embodiments of the present invention are able to generate oil having a yield of 1.4 lb/Bu. The methods and the systems disclosed herein also provides valuable byproducts, such as white fiber (for secondary alcohol production and paper industry), high value proteins meal (gluten meal, spent yeast and germ protein), glycerol, organic plant food, and animal nutrient diet food.

Some of features of the systems in accordance with some embodiments of the present invention are described in the following. Germ separating/recovering and dewater milling processes are included in some systems, which facilitates the germs particles to be separated from the fiber and to be broken up such that the oil from protein cell is able to be released for producing pure corn oil.

FIG. 5A illustrates a back-end oil recovery system 50A having a protein and white fiber recovery process. The system 50A includes liquid/solid separating 72, dewater milling 51, and germ/fiber separating 52. Similarly, FIG. 6A illustrates a front-end oil recovery system 60A having a protein and white fiber recovery process. The system 60A includes processes of liquid/solid separating 72 and germ/fiber separating 52. The processes 50A of FIGS. 5A and 60A of FIG. 6A provide advantageous features. For example, both processes 50A and 60A include a fiber purifying 53 to separate the protein and oil from the fiber, such that pure white fibers are able to be produced for secondary alcohol production or paper industry.

Oil emulsion and protein mixture are formed in a whole dry mil process, which affects the oil yield and protein purity. In some embodiments, oil/protein emulsion breaking process is included, such that the oil yield and the protein purity are able to be increased. For example in the process 50 of FIGS. 5 and 50A of FIG. 5A, a back-end oil recovery system contains pre-oil/protein separating 55, oil/protein emulsion breaking 56, oil purifying 54, and syrup polishing 57 are included to break the bonds between the oil and protein by using a centrifugal force, such that pure corn oil and higher protein meals are produced after fermenting 23. Similarly in the processes of 60 of FIGS. 6 and 60A for FIG. 6A having a front-end oil recovery system (oil recovering 47 and oil polishing 48 before the fermenting 23) are included to break the bonds between oil and protein by using a centrifugal force, such that pure corn oil and higher protein meals are produced. The 60 and 60A processes also include pre-oil/protein separating 55, oil/protein emulsion breaking 56, and syrup polishing 57 in the back end processes.

In some embodiments, (e.g., processes 50 of FIG. 5, 50A of FIG. 5A, 60 of FIG. 6, and 60A of FIG. 6A.), recovering glycerol and inorganic salt are included, which is referred to as Inorganic Process. There are about 1.5 lb./Bu of glycerin and 0.5 lb./Bu inorganic salt (rich in potassium and phosphate) in syrup. In some embodiments, glycerol recovering 58 and inorganic salt recovering 59 are included to separate/recover glycerol and inorganic salt (as organic plant food) from high concentrate syrup.

More details in accordance with the embodiments of the present invention are described below. There are generally two processes to recover oil. One of the two processes includes recovering oil in a front-end system before fermenting, such as processes 60 of FIG. 6 and 60A of FIG. 6A. The other process includes a back-end oil recovering system, such as processes 50 of FIG. 5 and process 5A of FIG. 5A. The front-end oil recovering system is able to provide higher oil quality (light color and low FFA) and give higher % of alcohol yield. Nonetheless, the front-end oil recovering system takes a higher capital investment.

In contrast, the back end oil recovery system has a lower oil quality (dark color and high FFA) and has a lower % of alcohol yield. However, lower capital investment is needed for the back-end oil recovering system.

Four exemplary processes in accordance with some embodiments are disclosed, which are able to be used individually, separated, or combined in any manners and in any sequences on the typical dry mill plants, such that valuable byproducts, such as oil, protein, white fiber, glycerin, inorganic salt, and nutritious high concentrated syrup with various quality and quantity are able to be produced.

In the back-end oil recovering process 50 of FIG. 5, oil/protein emulsion breaking and glycerin and inorganic salt recovering from de-oil and de-protein high concentrated syrup in the back-end process are included. The back-end oil recovering process 50A of FIG. 5A includes all four processes, including (1) oil/protein emulsion breaking, (2) glycerin and inorganic salt recovering, (3) germ recovering and dewater milling, and (4) fibers purifying in the back-end oil recovering system.

In the front-end oil recovery process, such as process 60 of FIG. 6, oil/protein emulsion breaking and glycerin and inorganic salt recovering from de-oil and de-protein high concentrated syrup in the front-end process are included. The front-end oil recovering of 60A of FIG. 6A includes all four processes, including (1) oil/protein emulsion breaking, (2) glycerin and inorganic salt recovering, (3) germ recovering and dewater milling, and (4) fibers purifying in the front-end oil recovering system.

Selective yields are discloses below. Typically, a conventional dry milling process is able to have a yield of 15.6 lb./Bu of DDGS. Using the dry milling processes with a back-end oil recovering system in accordance with some embodiments of the present invention, yields of 0.5 lb./Bu of oil and 15.1 lb./Bu of DDGS are able to be obtained. Further, a back-end oil recovery system with oil/protein emulsion breaking in accordance with some embodiments is able to have yields of 0.8 lb./Bu of oil, 3 lb./Bu of protein meal, and 11.8 lb./Bu of DDGS. Furthermore, a back-end oil recovery system with glycerin and inorganic salt separating in accordance with some embodiments is able to have yields of 0.8 lb./Bu of oil, 3 lb./Bu of protein meal, 1.5 lb./Bu of glycerin, 0.5 lb./Bu of inorganic salt, and 9.8 lb./Bu DDGS. Additionally, a back-end oil recovery system with germ recovering and dewater milling in accordance with some embodiments is able to have yields of 1 lb./Bu of oil, 5 lb./Bu of protein meal, 1.5 lb./Bu of glycerin, 0.5 lb./Bu inorganic salt, 7.6 lb./Bu DDGS. Moreover, a back-end oil recovery system with a fiber purifying process in accordance with some embodiments have yields of 1.2 lb./Bu of oil, 6 lb./Bu of protein meal, 1.5 lb/Bu of glycerin, 0.5 lb/Bu of an inorganic salt, 3 lb/Bu syrup, and 3.4 lb/Bu white fibers.

A front grinding and front oil recovery system of a dry milling system in accordance with some embodiments is able to generate 0.5 lb./Bu of oil, 14.6 lb./Bu of DDGS, and 2% of alcohol yield increase. Further, a front grinding and front oil recovery system of a dry milling system with an emulsion breaking in accordance with some embodiments is able to have yields of 1.0 lb./Bu of oil, 3 lb./Bu of protein meal, 11.1 lb./Bu of DDGS and 2% alcohol yield increase. Furthermore, a front grinding and front oil recovery system of a dry milling system with an oil/protein emulsion breaking in accordance with some embodiments is able to have yields of 1.0 lb./Bu of oil, 3 lb./Bu of protein meal, 11.1 lb./Bu of DDGS and 2% alcohol yield increase. Moreover, a front grinding and front oil recovery system of a dry milling system with a process of glycerin and inorganic salt separating in accordance with some embodiments is able to have yields of 1.0 lb./Bu of oil, 3 lb./Bu of protein meal, 1.5 lb./Bu of glycerin, 0.5 lb./Bu inorganic salt, 9.1 lb./Bu DDGS, and 2% alcohol yield increase. Further, a front grinding and front oil recovery system of a dry milling system with germ recovering and dewater milling in accordance with some embodiments is able to have yields of 1.2 lb./Bu of oil, 5 lb./Bu of protein meal, 1.5 lb./Bu of glycerin, 0.5 lb./Bu of inorganic salt, 6.9 lb./Bu of DDGS, and 2% alcohol yield increase. Furthermore, a front grinding and front oil recovery system of a dry milling system with fiber purifying in accordance with some embodiments is able to have yields of 1.4 lb./Bu of oil, 6 lb./Bu of protein meal, 1.5 lb./Bu of glycerin, 0.5 lb./Bu of inorganic salt, 2.5 lb./Bu of syrup and 3. lb./Bu of white fiber, and 3% alcohol yield increase. In the following some further aspects of the invention are disclosed.

In an aspect, a method of producing oil using a dry milling system comprises separating a whole stillage into a solid portion and a liquid portion after fermenting and grinding the solid portion after the separating to release oil from germs in kernels of grains. In some embodiments, the grinding comprises dewater milling. In other embodiments, the oil is recovered at oil recovering after fermenting. In some other embodiments, the liquid portion contains protein, oil, soluble solid, or a combination thereof. In some embodiments, the method further comprises oil and protein separating. In other embodiments, the oil and protein separating separates the liquid portion into an oily part and a protein part. In some other embodiments, the method further comprises fiber and protein dewatering generating DDG from the protein part. In some embodiments, the method further comprises recovering oil from the oily part from the oil and protein separating. In other embodiments, the recovering oil is performed without evaporating. In some other embodiments, the recovering oil is preformed before evaporating. In some embodiments, the method further comprises generating syrup having dry solid higher than 60%. In other embodiments, the grains comprise corn. In some other embodiments, the oil comprises corn oil.

In another aspect, a method of producing oil using a dry milling system comprises releasing oil from germs by dewater milling the germs after fermenting and recovering the oil after fermenting. In some embodiments, the method further comprises hammer milling before fermenting. In other embodiments, the method further comprises liquefying before fermenting. In some other embodiments, the method further comprises solid and liquid separating after the fermenting and before the dewater milling. In some embodiments, the method further comprises fiber and protein dewatering after the dewater milling. In other embodiments, the fiber and protein dewatering receives an input from both the dewater milling and oil and protein separating. In some other embodiments, the method further comprises oil and protein separating. In some embodiments, the method further comprises outputting an oil containing stream from the oil and protein separating. In other embodiments, the recovering the oil is performed without evaporating after fermenting. In some other embodiments, the recovering the oil is performed before evaporating.

In another aspect, a method of producing grain oil comprises separating oil and protein in thin stillage to an oil rich stream and a protein rich stream after fermenting, breaking oil and protein formed emulsion in the oil rich stream, and concentrating the oil in the oil rich stream from lower than 2% to higher than 20% of oil.

In some embodiments, the concentrating is performed using one or more two or three phase disc centrifuges. In other embodiments, the disc centrifuges comprise a nozzle centrifuge, a disc decanter, or a combination thereof. In some other embodiments, the method further comprises purifying the oil using a three phase centrifuge.

In another aspect, a method of separating proteins from a syrup comprises separating a light phase from a cake phase by density difference of a first syrup containing 10%~40% of dry solid, wherein the light phase contains emulsion having oil, proteins, and germ particles and wherein the cake phase contains proteins including spent yeast and germ protein, generating a de-oil and de-protein second syrup, and concentrating the second syrup to form a third syrup containing 80% of dry solid.

In some embodiments, the concentrating is performed using one or more three phase centrifuges. In other embodiments, the one or more three phase centrifuges comprise decanters, disc centrifuges, disc decanter centrifuge, or a combination thereof. In some other embodiments, the proteins comprise spent yeast, germ protein, or a combination thereof.

In another aspect, a method of separating glycerin and inorganic salt from a high concentration syrup comprises obtaining glycerin and inorganic salt from syrup containing 60%~80% of dry solid and forming animal feed with the syrup.

In another aspect, a dry milling system comprises a germ grinding unit coupling with a fermenting unit and after the fermenting unit in a processing sequence and an oil recovering unit coupling with the germ grinding unit.

In some embodiments, the system further comprises an emulsion processing unit. In other embodiments, the emulsion processing unit comprises oil and protein emulsion breaking. In other embodiments, the system further comprises a fiber processing unit. In some other embodiments, the fiber processing unit comprises a caustic treatments unit. In some embodiments, the fiber processing unit produces white fiber. In other embodiments, the system further comprises a glycerol recovering unit. In some other embodiments, the system further comprises an inorganic salt recovering unit. In some embodiments, the system further comprises a counter current washing system. In other embodiments, the oil recovering unit is before the fermenting unit in a processing sequence. In some other embodiments, the oil recovering unit is after the fermenting unit in a processing sequence. In some embodiments, the system further comprises one or more dewater milling units before the fermenting unit. In other embodiments, the system further comprises multiple dewater milling units coupled in series before the fermenting unit. In some other embodiments, the germ grinding unit comprises multiple grinding mills in series after the fermenting unit.

BRIEF DESCRIPTION OF THE DRAWINGS

Embodiments will now be described by way of examples, with reference to the accompanying drawings which are meant to be exemplary and not limiting. For all figures mentioned herein, like numbered elements refer to like elements throughout.

DETAILED DESCRIPTION OF THE PREFERRED EMBODIMENT

Figure 1:
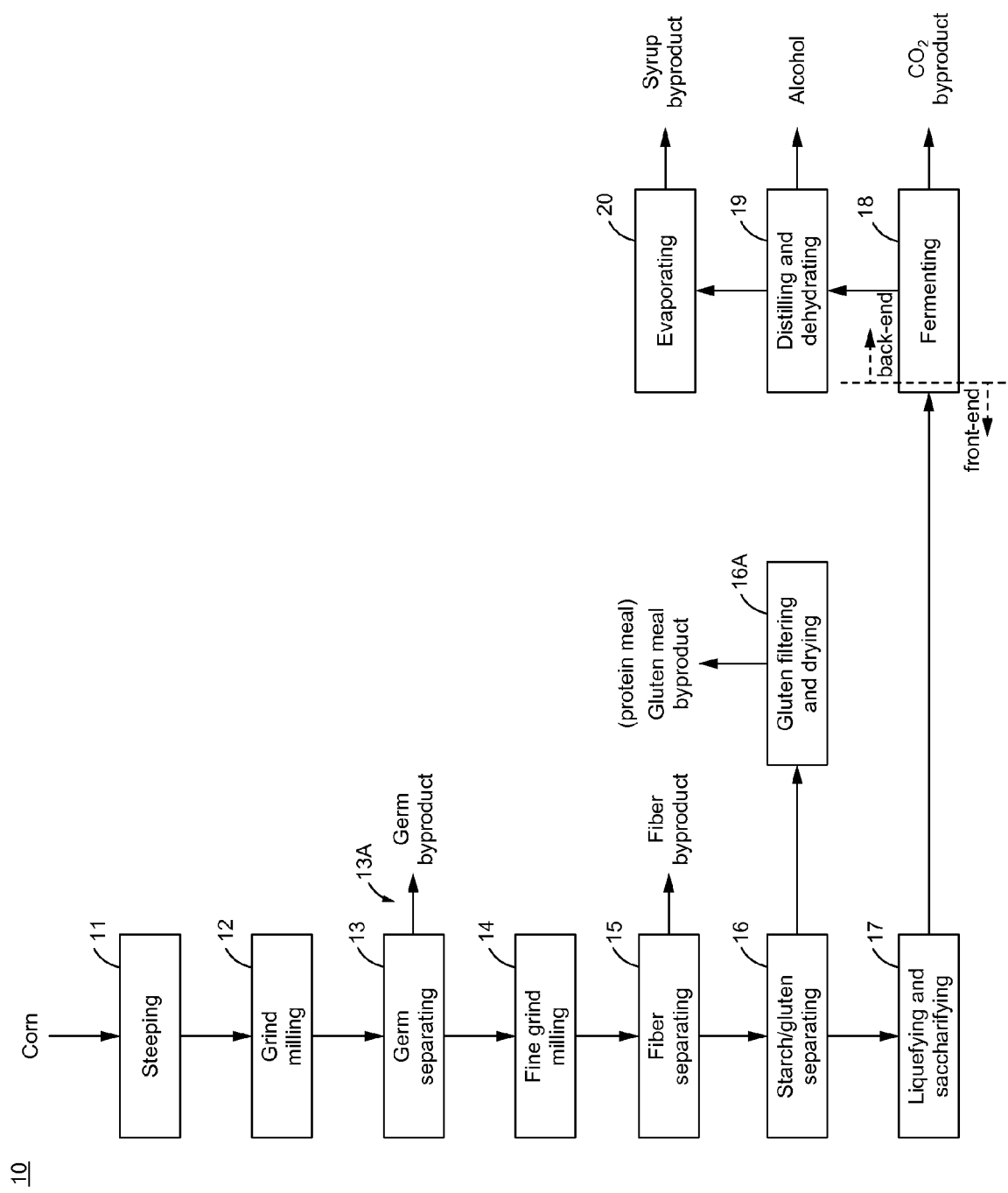
FIG. 1 is a flow diagram of a typical wet-milling process for producing ethanol and distiller's grains with soluble.

A typical dry milling alcohol plant produces only one byproduct, which is called DDGS containing about 29%~31% of protein, 11%~13% of oil and 4%~6% of starch. The DDGS yield is about 15.6 lb./Bu, which has around 4.7 lb./Bu of protein, 2 lb./Bu of oil and 0.8 lb./Bu of starch. DDGS generated at the typical dry milling plant has a low selling price even though it has a high protein and oil content. The low selling price of the DDGS generated at the typical dry milling plant is because that too many fibers are in the DDGS, which is only good as feed for animals like cow and not good for chicken or fish.

In some embodiments, the processes and/or devices of the present invention is able to separate the individual compounds/components in the DDGS to be in a more pure form and to become a more valuable byproduct, such as white fiber (less than 10% of protein, less than 3% of oil, and less than 2% of starch) for secondary alcohol feed stock, raw material for water resistant pulp for paper industry, proteins meal (more than 45% of protein, less than 3% of oil, and less than 2% of starch), corn oil, glycerin, inorganic salt, and syrup (as a nutrient for animal feed). Some embodiments of the present invention separate the DDGS into 5 parts including: (1) larger solid particles (having particle sizes larger than 300 micron), which is a combination of fiber (per-cap and tip-cap) bonded with some protein and starch, grit (fine fiber bonding with protein), and germ particles, contained in an oil drop protected by a protein cell wall inside the germ (The yield of the larger solid particles is about 6 lb./Bu with a composition of 28% of protein, 8% of oil, and 4% of starch); (2) protein portion containing mainly protein (gluten, spent yeast, and germ protein) with some fine fibers, which is bonded with starch and absorb oil in the fine fiber, (the protein portion is an insoluble solid having a density of 1.1 and has a particle size ranging from 5 micron to 300 micron; the yield for the protein portion is about 4 lb./Bu, and the protein portion has a composition of 45% of protein, 5% of oil, and 2% of starch); (3) very fine germ paste and oil/protein emulsion, which has a density around 1 and a particle size from submicron to 5 micron (very fine germ paste and oil/protein emulsion having a yield about 1.6 lb./Bu with a composition of 35% of protein, 30% of oil, and 2% of starch; (4) soluble solid that contains inorganic salt in corn, sugar, byproducts from fermentation (such as lactic acid, glycerol), and acetic acid (the yield is about 4 lb./Bu with a composition of 8% of protein, 7% of oil, and 5% of starch; (5) "free" oil, which is the oil that is able to be recovered by a centrifuge (the yield is about 1 lb./Bu).

In the following, four processes in accordance with some embodiments of the present invention are disclosed. These processes are able to be added to typical dry mill processes/systems, such that sharper separations among fiber, protein, and oil are able to be obtained and more pure valuable byproducts, such as white fiber, proteins (gluten, spent yeast, and germ), oil, glycerin, inorganic salts, and nutrients for animal feed are able to be produced.

Figure 5:
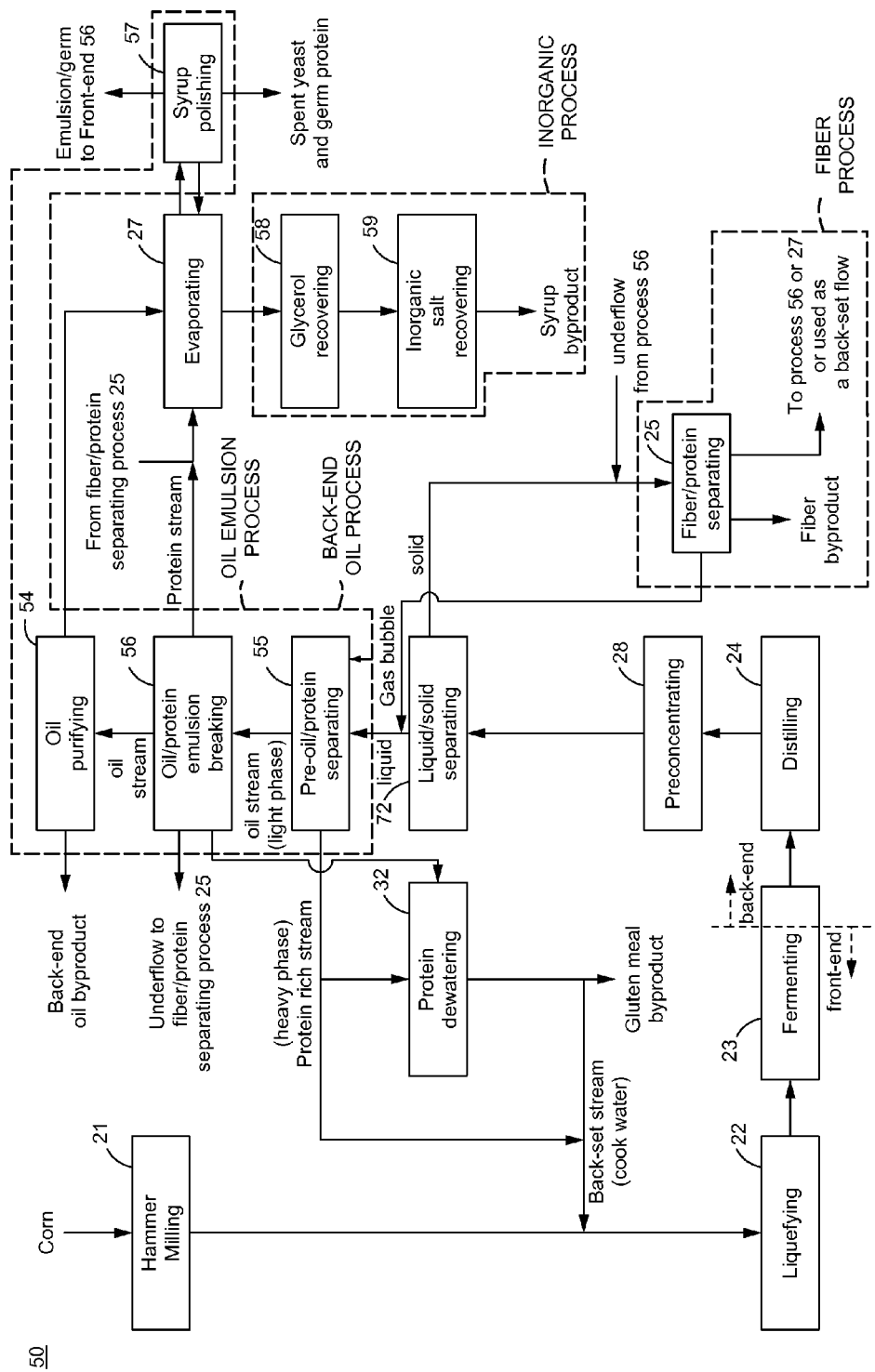
FIG. 5 is a flow diagram of a dry milling process with back end oil recovering and protein recovering in accordance with some embodiments of the present invention.
Figure 5A:
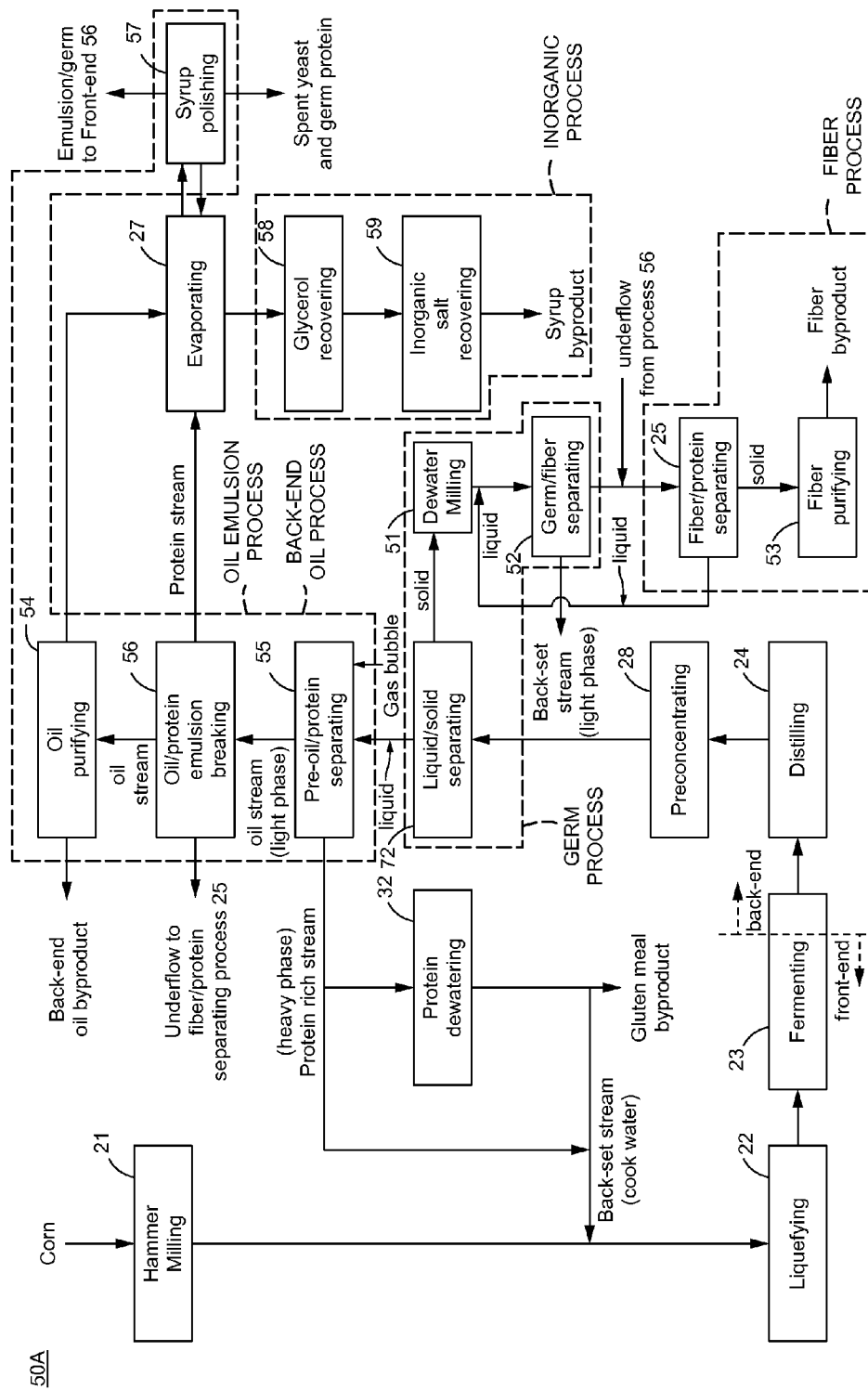
FIGS. 5A, 5B, and 5C are flow diagrams of dry milling processes with back end oil recovering, protein recovering, and white fiber recovering in accordance with some embodiments of the present invention.
Figure 5B:
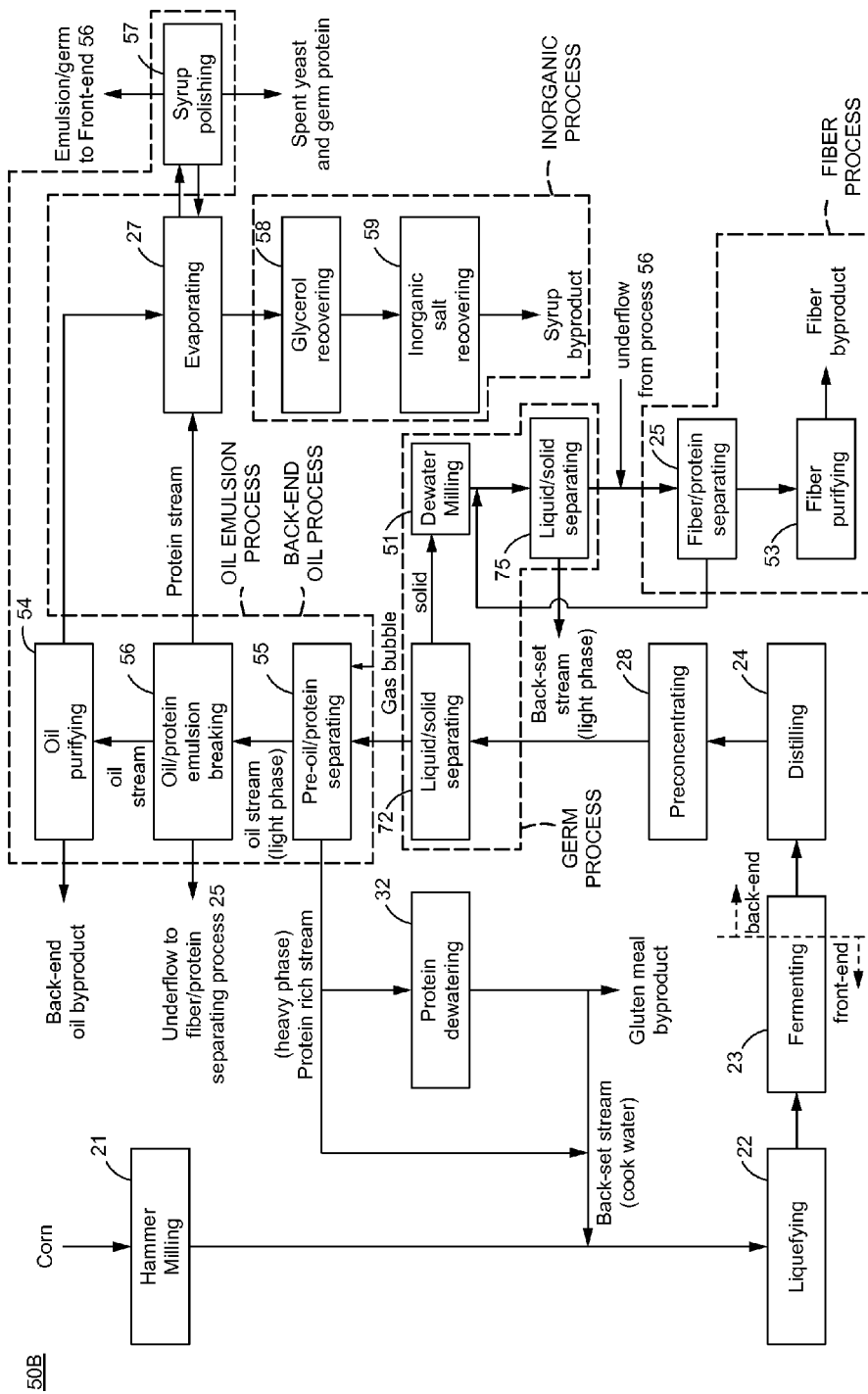
Figure 5C:
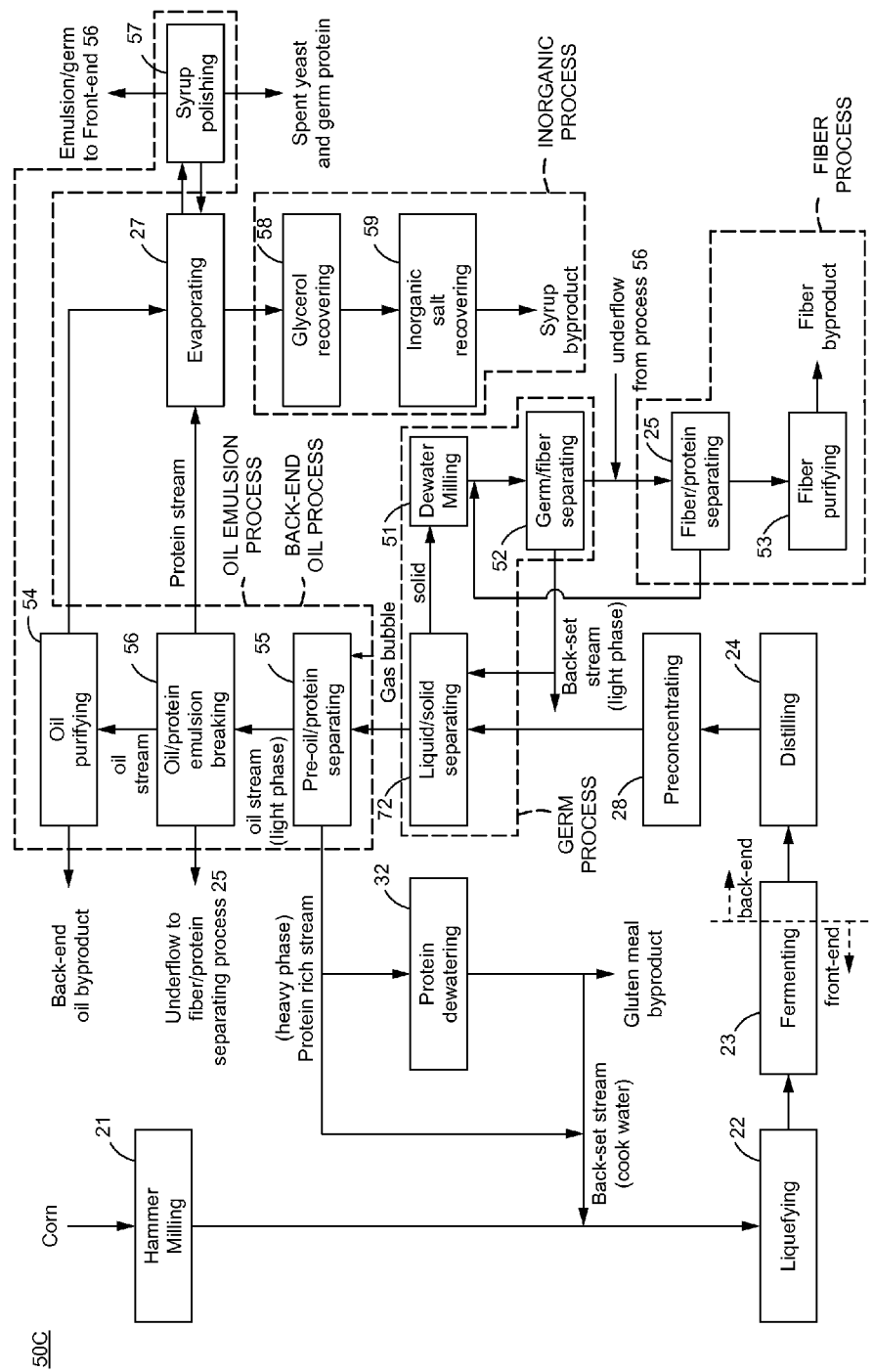
Figure 6:
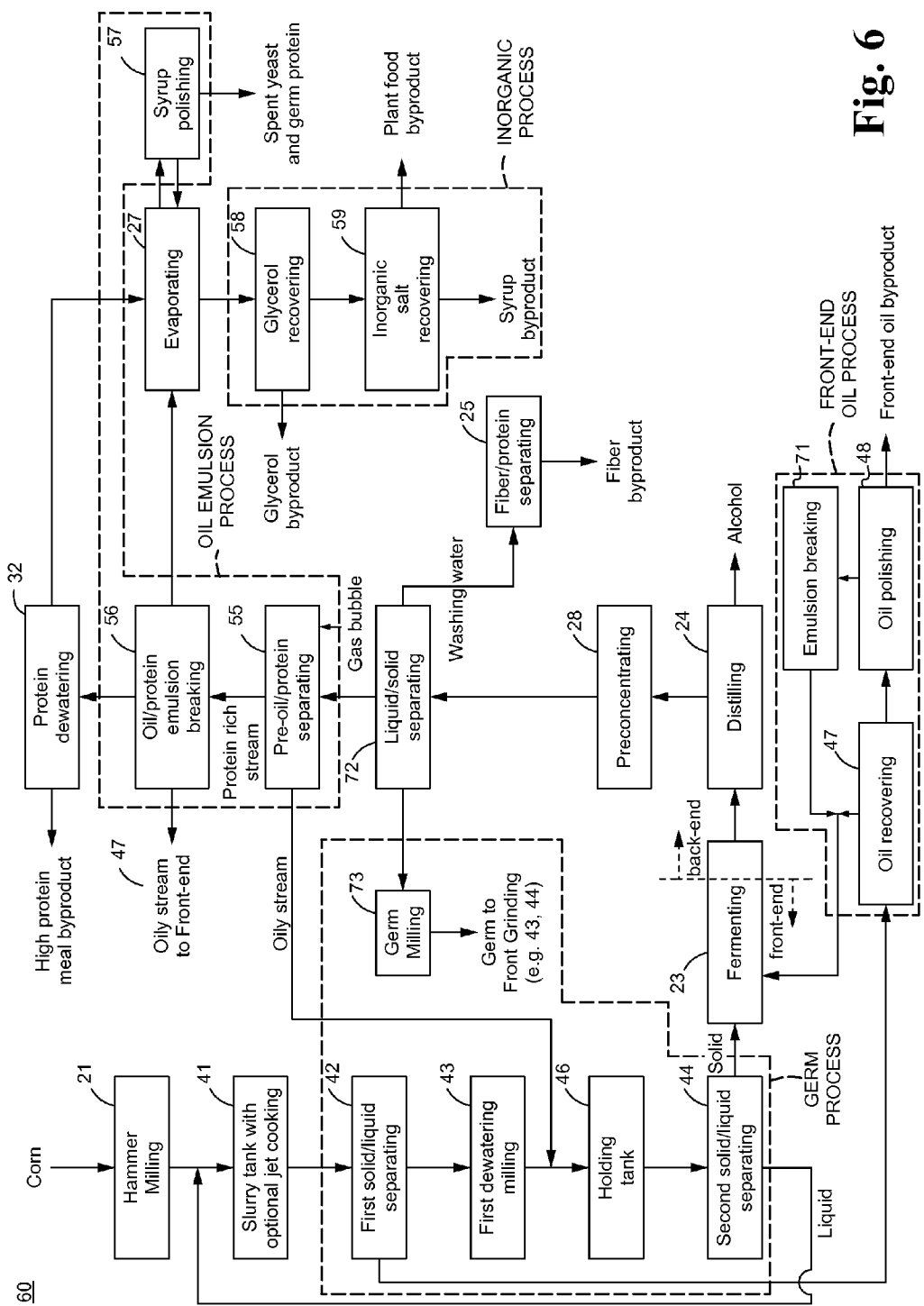
FIG. 6 is a flow diagram of a dry milling process with front end oil recovering and protein recovering in accordance with some embodiments of the present invention.
Figure 6A:
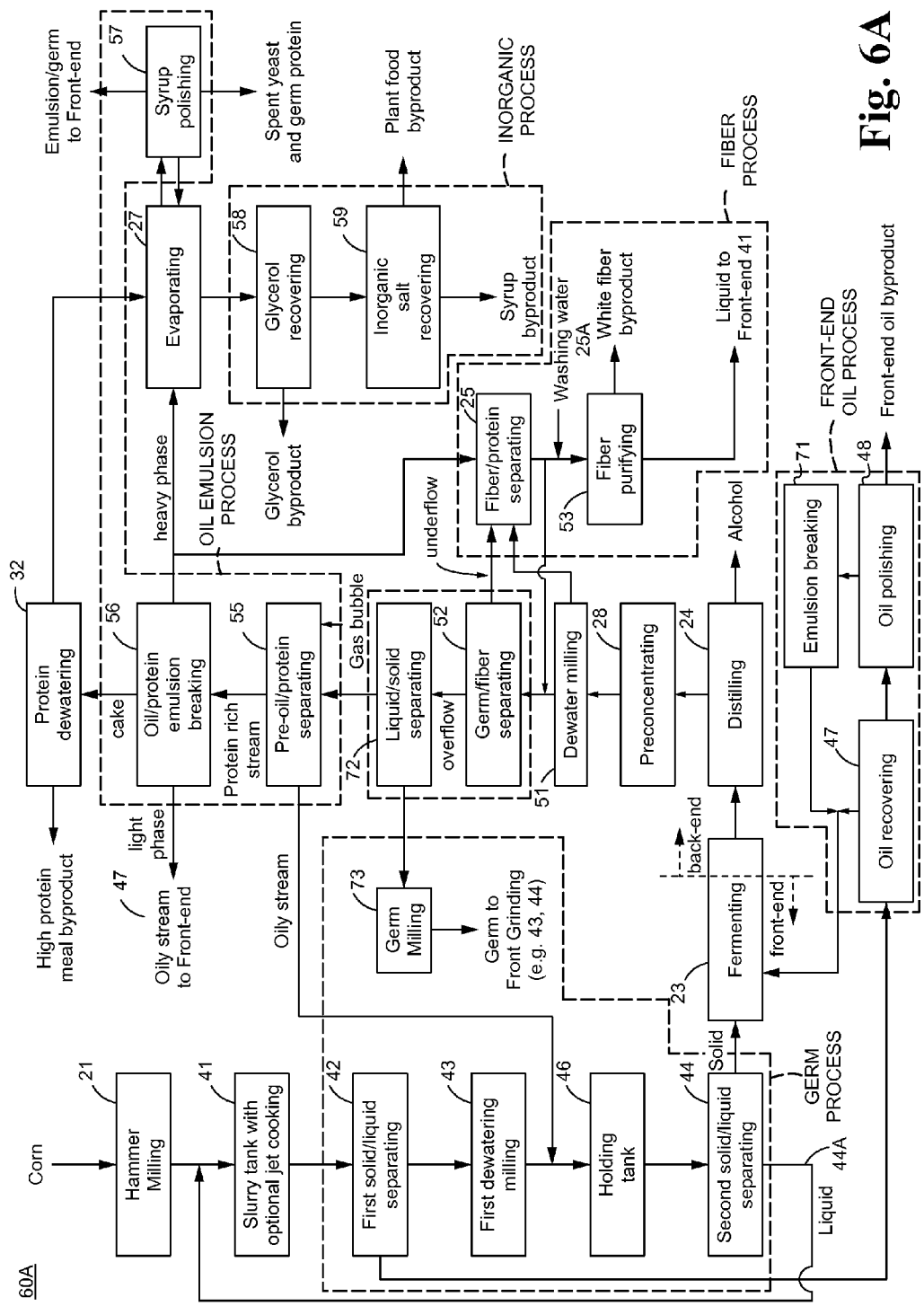
FIG. 6A is a flow diagram of a dry milling process with front end oil recovering, protein recovering, and white fiber recovering in accordance with some embodiments of the present invention.

The process 50A of FIG. 5A and process 60A of FIG. 6A include germ recovering/dewater milling processes in accordance with some embodiments of the present invention. The processes described above are able to release and recover more than 2 lb./Bu of germs in the whole stillage. The process 50A and 60A include solid/liquid separating 72, dewater milling 51, and germ/fiber separating 52, such that the germs from fiber are able to be separated and germ particles able to be to be broken up to release oil from the protein cells and to produce pure corn oil.

Further, the process 50A of FIG. 5A and process 60A of FIG. 6A include fiber purifying processes in accordance with some embodiments of the present invention. The fiber is able to be purified for white fiber production, which is able to be used for the secondary alcohol production or to be used in the paper industry. There are more than 20% of protein and 8% of oil bonding with the fiber in the DDG. The inclusion of the fiber purifying 53 is able to separate the protein and the oil from fiber, to produce pure white fiber for secondary alcohol production or paper industry, and also to increase the yield of oil and protein at the same time.

Furthermore, the processes 50 of FIG. 5, 50A of FIG. 5A, 60 of FIGS. 6 and 60A of FIG. 6A include oil/protein emulsion breaking processes in a whole dry milling system, which is able to increase the yield of oil and the purity of protein. In the back-end oil recovery system (recovering oil after fermenting), such as process 50 and 50A, pre-oil/protein separating 55, oil/protein emulsion braking 56, oil purifying 54, and syrup polishing 57 are included. The processes of oil/protein emulsion braking 56 and oil purifying 54 at the back-end are used to break the bonds between the oil and protein by using centrifugal force to produce pure corn oil and protein meals. Similarly in the front-end oil recovery system, such as the processes 60 and 60A, the pre-oil/protein separating 55, oil/protein emulsion breaking 56, protein dewatering 32 and syrup polishing 57 are included. The oil recovering 47 and oil polishing 48 at the front-end are used to break the bonds between oil and protein by using a centrifugal force to produce pure corn oil and protein meals.

Moreover, the processes 50 of FIG. 5, 50A of FIG. 5A, 60 of FIGS. 6 and 60A of FIG. 6A include glycerol and inorganic salt recovering processes in accordance with some embodiments of the present invention. There are about 1.5 lb./Bu of glycerin and 0.5 lb./Bu inorganic salt in the syrup. The glycerol and inorganic salt recovering processes disclosed herein are able to separate/recover glycerol and inorganic salt (as organic plant food) from high concentrate syrup.

More details of the exemplary embodiments are described below. The embodiments disclosed herein mainly include a front grinding and front oil recovery system, such as the processes 60 of the FIG. 6 and the 60A of the FIG. 6A, and a back-end oil recovery system, such as the processes 50 of FIGS. 5 and 50A of FIG. 5A.

In some embodiments, the process 50 includes the oil/protein emulsion breaking 56, glycerol recovering 58 and inorganic salt recovering 59 from a concentrated syrup. The process 50A includes the oil/protein emulsion breaking 56, glycerol recovering 58 and inorganic salt recovering 59, germ/fiber separating 52, dewater milling 51, and fiber purifying 53.

In some embodiments, the process 60 adds the oil/protein emulsion breaking, front-grinding and glycerol and inorganic salt stage recovering, and front oil recovering to a system that is described in the process 40. In some embodiments, the process 60A adds oil/protein emulsion breaking, glycerol and inorganic salt recovering, germ recovering/dewater milling and fiber purifying in a front grinding system to the oil recovering system of process 40. The processes will be described in more detail in following sections.

Generally, there are about 3 lb./Bu of gluten protein and 1 lb./Bu of germ protein inside the corn kernel. There is also about 0.8 lb./Bu of yeast protein from fermentation. Thus, there are total about of 4.8 lb./Bu of total protein inside the whole stillage. A protein recovery process is able to produce protein meal with 50% protein purity by including oil/protein separating 31, protein dewatering 32 and protein drying 32 in addition to the processes that are performed in a typical dry milling system. With the process 30 described above, the protein yield is still only about 3 lb./Bu of protein meal at 50% protein content, so only 33% of protein inside whole stillage is recovered. Although there are about 2 lb./Bu oil in the corn kennel, both the back-end oil recovery system (such as the process 20) and the front-end oil recovery system (such as the process 40) are only able to have a yield of 0.5 lb./Bu, which shows that only about 25% of oil is recovered.

In some embodiments, the processes of the present invention increase the yields of oil and protein by separating/recovering oil from the germs and separating/recovering oil and protein from fibers that are bonded with protein and oil inside the DDGS. In addition, some embodiments of the present invention increase the purity of fibers by separating/recovering the protein and oil, such that more valuable white fiber are able to be produced instead of DDGS.

Figure 2:
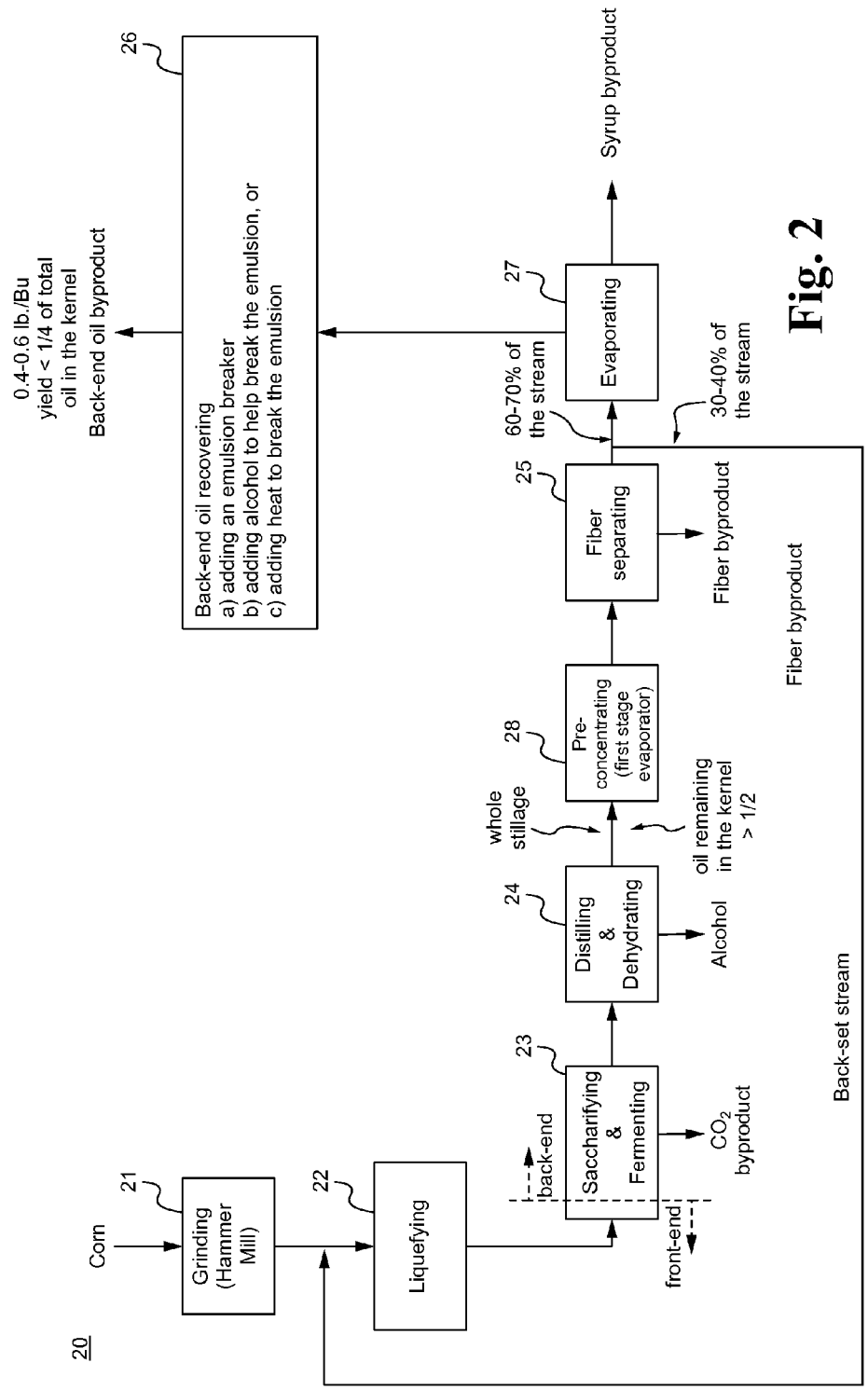
FIG. 2 is a flow diagram of a typical dry-milling process for ethanol production and back-end oil recovery.
Figure 3:
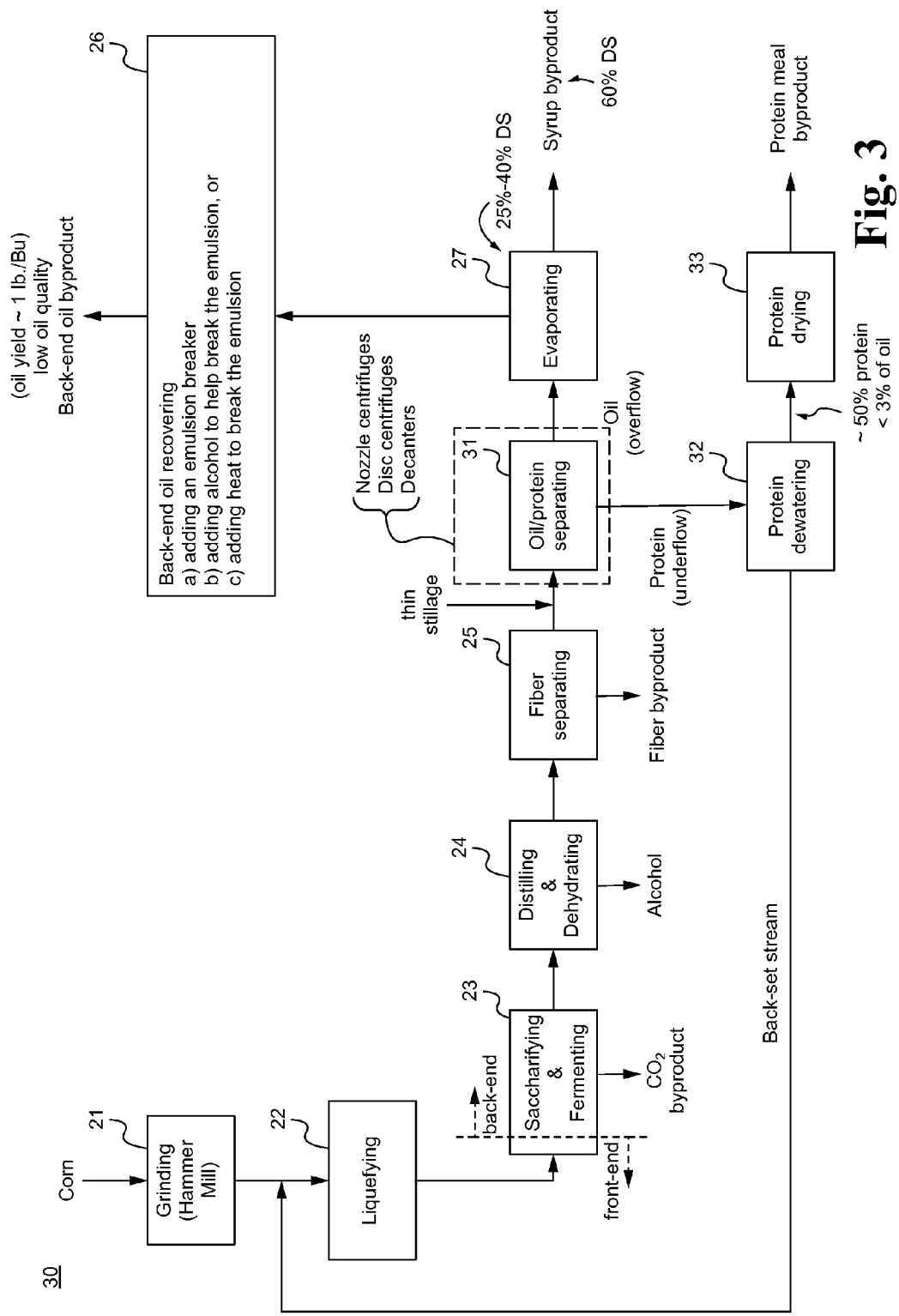
FIG. 3 is a flow diagram of a typical dry-milling process for ethanol production and back-end oil and protein recovery.

The process 50 of FIG. 5 is able to a) increase protein yield and purity as well as separating more valuable proteins (spent yeast and germ protein) from gluten protein, b) increase the oil yield, c) produce other two valuable byproducts including glycerin and inorganic salt. The process 50 of FIG. 5 includes the additional processes of solid/liquid separating 72, pre-oil/protein separating 55, oil/protein emulsion breaking 56, oil purifying 54, and syrup polishing 57 when the process 50 is compared with the dry mill process that is described in the process 20 in FIG. 2.

In the process 50, the whole stillage from distilling 24 is able to be optionally preconcentratd in preconcentrating 28, such that the solid content is able to be increased from about 13% of DS to 15%~25% of DS before sending the substance to the solid/liquid separating 72 to separate the solid (mainly fiber, germ and grit) from the liquid (mainly protein, fine fiber, small germ particle, starch, oil and soluble solid).

The solid phase from this solid/liquid separating 72 of the process 50 is able to be mixed with the underflow (de-oiled protein rich stream) from the oil/protein emulsion breaking 56 to form a mixture stream. Next, the mixture stream is sent to fiber/protein separating 25, such that fibers and proteins are able to be removed to produce DDG cake. The DDG cake is able to be mixed with the syrup from evaporating 27 to produce DDGS as a byproduct. The thin stillage from fiber/protein separation step 25 is able to go to back to evaporating 27 or pre-oil/protein separation step 55 or back set.

The liquid phase from solid/liquid separating 72 of the process 50 is able to be optionally mixed with the thin stillage from fiber/protein separating 25 forming a mixture, which is able to be sent to pre-oil/protein separating 55, such that the oil and protein slurry are able to be separated into two streams including an oil rich stream and a protein rich stream.

The oil and protein slurry in the pre-oil/protein separating 55 of the process 50 contains about 2% insoluble protein and 1% oil, which is able to be separated into two layers in a simple holding tank with several hour of holding time. The light layer (oil rich stream) contains more oil (around 1.3% to 1.7% of oil) and less protein (1.3% to 1.7%). The heavy phase (protein rich stream) containing less oil (0.3 to 0.7%) and more protein (2.3 to 2.7%) is at the bottom of settle tank. The heavy phase (protein rich stream) from the pre-oil/protein separating 55 is able to be sent to the front-end as a back-set stream, which is used as a part of cook water or is able to be optionally sent to protein dewatering 32 to produce protein meal. The overflow from protein dewatering 32 is able to be sent to the front-end as a back-set stream, which is used as part of the cook water. The light phase (oil rich stream) from the oil/protein separating 55 is able to go to oil/protein emulsion breaking 56.

In some embodiments, the plant includes large thin stillage holding tank, so that more than four hour holding time is able to be used for this pre-oil/protein separating 55 of the process 50. In some embodiments, incline plate settler is used to increase the separation area with smaller holding/settle tank. In some embodiments, gas (air or $CO_2$) in a form of fine bubble is used to speed up this pre-oil/protein separating 55. Coagulated agents and commercial air floatation units are used in some embodiments.

In a typical dry milling process, the thin stillage is normally spitted into two streams by a simple volume splitting process. Each of the streams contains same oil concentration (about 1% oil in thins stillage). About 30%~50% of stream is recycled back as cook water to the slurry tank to cut the usage of fresh water and save evaporating energy. Other 50%~70% of the stream is sent to an evaporator to be concentrated to about 30~40% DS as a syrup. Both streams have same amount of oil and protein content. The oil in syrup is not recovered unless other back-end oil recovery system is instilled. The syrup is also cannot be concentrated to be more than 40% of DS, because too much of the protein in the solution is able to foul the evaporator.

In the oil/protein emulsion breaking 56 of the process 50, higher speed disc centrifuges such as two or three phase nozzle centrifuge are used to break the bonds between the oil and protein by density difference (oil is 0.9 gram/ml and protein is 1.15 gram/ml). All of the oil, oil/protein emulsion, germ particles (depending on the density of both liquid and germ particle) that are lighter than the liquid are separated from the proteins and fine fibers. The light phase stream contains more oil, oil/protein emulsion, and germ particles in the liquid stream are discharged from the oil/protein emulsion breaking 56. In the oil/protein emulsion breaking 56, the heavy phase stream (containing more proteins and fine fibers) that is heavier than the liquid are separated from oil/emulsion/germ stream as heavy phase discharge stream. The top layer of the light liquid phase stream (with about 30 to 70% of liquid) contains mainly oil, oil/emulsion, and fine germ particles. The heavy liquid phase stream (with about 30 to 70% of liquid) contains mainly proteins and fine fibers and sometimes with germ particles depending on the size of the germs and the density of the liquid. A person of ordinary skill in the art appreciates that the liquid splitting ratio is able to be in any ratio from 5:95, 10:90, 30:70, 50:50 to 80:20.

The light phase from oil/protein emulsion breaking 56 contains about 30 to 70% oil that is sent to oil purifying 54 to produce pure corn oil. The heavy phase from oil/protein emulsion breaking 56 is able to be optionally sent to protein dewatering 32 to recovery the protein or directly sent to evaporating 27 when the protein dewatering 32 is not instilled.

When using a three phase decanter in the oil/protein emulsion breaking 56 of the process 50, a three phase disc decanter is able to be used. The cake phase from three phase centrifuges/decanter is able to contain mainly corn gluten with some germ and spend yeast. The cake with protein is able to be sent to a protein dryer (not show) to produce protein meal (with 50% protein and less than 3% oil) or is able to be sent to DDGS dryer to produce DDGS as a byproduct.

When a three phase nozzle centrifuge is used in the oil/protein emulsion breaking 56 of the process 50, the underflow is heavy protein slurry instead of cake. The heavy protein slurry is mixed with the solid phase from the solid/liquid separating 72 to the decanter at fiber/protein separating 25 to produce DDG cake, which is then mixed with syrup to produce DDGS byproduct. The overflow from fiber/protein separating 25 is able to be optionally sent to the oil/protein emulsion breaking 56, to front-end as a back-set flow, and/or to evaporating 27.

The heavy phase discharge from the oil/protein emulsion breaking 56 and oil purifying 54 of the process 50 with the overflow from the fiber/protein separating 25, optionally, are able to be sent to evaporating 27 to be concentrated to around 20% to 40% of total solid before the content is sent to syrup polishing 57. The light phase stream from this syrup polishing 57 (containing mainly emulsion and fine germ particles with high oil content (more 30% of oil)) is able to go through any emulsion breaking process (such as using heat, chemical, or alcohols to break the emulsion) to recover more oil or is sent to a DDGS dryer to become part of the DDGS. The heavy phase stream from syrup polishing 57 (containing mainly soluble solid from corn and fermenting byproducts, such as glycerol) are sent to the evaporating 27 to be concentrated to about 50%~80% DS and to produce syrup as a byproduct. The underflow/cake flow of the syrup polishing 57 contains mainly germ protein and spent yeast, which is able to be mixed with protein cake (mainly gluten) from protein dewatering 32 or optionally sold as a high value protein meal for fish. Alternatively, the underflow/cake of the syrup polishing 57 is mixed with the fiber cake that is received from fiber/protein separating 25 to produce DDGS byproducts.

The deoil and deprotein syrup from the syrup polishing 57 of process 50 is able to be further concentrated to contain 80% of DS, because the protein (which forms scale in evaporator) is removed. This high percentage of DS syrup with very high content of free oil and insoluble protein is ideal for making organic plant food. The syrup polishing 57 is able to be repeated several times during a series of evaporating processes to further recover more proteins and oil/emulsion as long as keeping the protein content low in the syrup, so the viscosity of the syrup maintains low and not fouling the evaporator. Next, the syrup is able to be concentrated to be as high as 80% of DS with a low/the lowest oil and protein content. In an example, after the second stage evaporator (a second evaporating process), the syrup is fed to a centrifuge and generates light phase and a protein cake. The light phase contains oil/emulsion/germ having 11.3% of protein, 61.5% of oil, and 0.79% of starch. The protein cake contains 38.9% of protein, 0.95% of oil, and 2.79% of starch. The de-oil and de-protein separated syrup has 22% of DS. Next, the syrup is sent to a third stage evaporating 27 for removing more water followed by syrup polishing 57. The light phase contains 22.5% of protein, 42.4% of oil, and 1.68% of starch. The protein cake phase contains 31.4% of protein, 0.14% of oil, and 4.08% of starch. The separated de-oil and de-protein syrup has 29.7% of DS The light phase from the syrup polishing 57 contains oil/emulsion/small germ particles and cake (containing mainly yeast and low oil germ protein). In some embodiments, a three phase decanter or a disc centrifuge is used at the syrup polishing 57, because of the high viscosity of syrup that needs a much higher G force centrifuge (e.g., disc decanter with two disc stock in series design, which is able to be used to provide a better separation). In some other embodiments, syrup polishing 57 uses a microfiltration device. The light phase discharge (the oil/emulsion/small germ paste) of the syrup polishing 57 contains 30%~50% of oil depending on syrup concentration and the centrifuge operation. The oil is sent to emulsion breaking 56 to break the emulsion and recover more oil.

The protein cake from the protein dewatering 32 and syrup polishing 57 of process 50 that contains less than 3% of oil is able to be combined to produce a high protein high value meal (about 50% protein) or sold separately as gluten meal and yeast/germ protein.

After the fiber/protein separating 25 of the process 50, another factor that affects the oil yield is how to effectively break the bonds between oil and protein in the syrup. The product content is able to be adjusted based on predetermined factors and the needs of the factories. Minimizing the oil in the syrup is selected when the dry milling plant only produces DDGS as a byproduct. Minimizing the percentage of oil in both the syrup and protein is selected when the dry mill plant produces both DDGS and protein meal. The oil/protein emulsion breaking 56 is able to be mainly for breaking the bonds between oil and protein and cutting down oil loss to the syrup. The syrup polishing 57 is mainly for cutting down oil loss to both syrup and protein stream.

The de-oil and de-protein syrup after syrup polishing 57 is able to be concentrated up to 80% of DS without fouling the evaporator. The highly concentrated (free of oil and protein) syrup contains about 15%~20% inorganic salt, 35%~45% of sugar (such as sugar that remains not been fermented, maltose, glucose and fructose), and 35%~45% fermenting byproducts (such as lactic acid and glycerol), which are able to be recovered by going through glycerol recovering 58 and inorganic recovering 59 to recover/remove the glycerol and separate the inorganic salt. The glycerol is valuable chemical in industry and the inorganic salt is able to be used as organic plant food. The vacuum distillation or combining micron filtration and ultrafiltration is able to be used on the glycerol recovering 58. Any liquid/solid separation device, such as screen bowl decanter centrifuge, is able to be used at the inorganic salt separating 59. Holding the concentrated syrup on a cool place for longer duration is able to help the growth of the crystal of the inorganic salt to a larger size and make inorganic salt separating 59 much easier.

The syrup after glycerol recovering 58 and inorganic salt separating 59 contain mainly animal undulation material that is commonly called "unknown growth factor," which is able to be used as an animal diet supplement or to be mixed with fiber DDG and to be sold as DDGS. In some embodiments, the syrup is also able to be recycled back to the front-end to increase the alcohol yield, because some sugar inside is still able to be used for producing extra alcohol.

The processes/steps described in the process 50 are optional and all the processes/steps are able to be performed in different orders. Additional steps/processes are able to be added. For example in some embodiments, the system does not include glycerol separating 58 when glycerin and inorganic are not to be recovered. In another example, the system does not include the syrup polishing 57, such that the system is able to produce 3 lb./Bu gluten meal. In some other embodiments, the pre-oil/protein separating 55, oil/protein emulsion breaking 56, and oil purifying 54 are included, such that the yield of oil is able to be around 0.6~0.8 lb./Bu. While adding pre-oil/protein separating 55 or oil/protein emulsion breaking 56 (with a back-end oil recovering system or with syrup polishing 57), the oil yield is able to be around 0.8~1 lb./Bu.

In some embodiments of the present invention, the germ separating and dewater milling (the liquid/solid separating 72, dewater milling 51, and germ/fiber separating 52) with the fiber purifying (fiber purifying 53) are able to be further included in the process 50 in FIG. 5 to recover germ and dewater milling germ, such that the protein cell wall is able to be broken up and therefore the oil is able to be released. In addition, fiber purifying 53 is able to be added to the process 50 to produce white fiber.

In some embodiments, the process 50A includes the processes in the process 50 with additional liquid/solid separating 72, dewater milling 51, germ/fiber separating 52 and fiber purifying 53. The additional processes in the process 50A are after fermenting 23 and before fiber/protein separating 25. In the process 50A, corns go through hammer milling 21, liquefying 22, fermenting 23, and distilling 24 and preconcentrating 28, which are processes that are also included in the process 50. The bottom layer of the distilling 24 (whole stillage) of the process 50A contains fiber and germ particles, corn proteins, yeasts, and byproducts from the fermenting 23 and ash from corn. The whole stillage with 12%~14% of DS is able to be optionally going through the first evaporator (the preconcentrating 28) to be concentrated to 15%~25% of DS. Next, the whole stillage or concentrated whole stillage is sent to liquid/solid separating 72 to separate the solid (mainly fiber, germ and grit) from the liquid (mainly protein, fine germ and starch particle, oil, fine fiber, and soluble solid.)

The solid phase of the liquid/solid separating 72 is sent to dewater milling 51 to break the germ and grit particles and release the oil and starches. The solid phase of the dewater milling 51 is mixed with the liquid phase from the fiber/protein separating 25 and sent to germ/fiber separating 52. The light phase from germ/fiber separating 52 that contains mainly germ particle with liquid is able to be sent back to the front-end as part of cook water (back set stream). The heavy phase from germ/fiber separating 52 is mixed with the underflow stream from the oil/protein emulsion breaking 56 and is sent to fiber/protein separating 25. The solid phase from fiber/protein separating 25 is sent to DDG S dryer to produce DDGS byproduct (not shown in the figure for clarity) or is continually going through the fiber purifying 53 to produce white fiber for producing secondary alcohol or water resistant pulp.

In some embodiments, the liquid phase of the solid/liquid separating 72 is sent to pre-oil/protein separating 55, then the rest of the processes are able to be the same as process 50. For example, the oil and protein slurry at the pre-oil/protein separating 55 is able to be split into two streams including an oil rich stream and a protein rich stream. The protein rich stream with the optional protein dewatering 32 is able to produce protein cake or is able to be sent back to the front-end as a back-set stream of the cook water. The oil rich stream is able to go through oil/protein emulsion breaking 56 and oil purifying 54 to produce pure corn oil.

The heavy phase from oil/protein emulsion 56 and oil purifying 54 are able to be sent to evaporating 27 to be concentrated to contain 20%~40% of DS. The concentrated syrup is sent to syrup polishing 57 to recover emulsion/germ as a light phase, fine protein (spend yeast and germ protein) as a cake phase, and the de-oil and de-protein syrup as a heavy phase. The de-oil and de-protein syrup is able to be concentrated up to 80% of DS. Next, glycerol separating 58 (after evaporating 27) is able to recover glycerol followed by inorganic salt separating 59 to recover inorganic salt The germ recovering/dewater milling ("germ process") in some embodiments of the present invention are able to include the solid/liquid separating 72, dewater milling 51 and germ/fiber separating 52.

The process 50B is able to be similar to the process 50A. In some embodiments, the germ/fiber separating 52 is replaced by solid/liquid separating 75 in the process 50B. The process using solid/liquid separating 75 in the process 50B, which has an oil yield about 0.1 lb./Bu lower than the oil yield of the process 50A, because germ/fiber separating is not used.

Process 50C of FIG. 5 C illustrates embodiments having solid/liquid separating 72, dewater milling 51 and germ/fiber separating 52 that are set up differently from the process of 50A. The whole stillage is able to be sent to solid liquid separating 72. The solid phase is able to be sent to dewater milling 51 to release oil from the germs. At the dewater milling 51, the ground solid is mixed with a liquid from fiber/protein separating 25 and is able to be sent to germ/fiber separating 52. The light phase of the germ/fiber separating 52 that contains unbroken germ particle is able to go back to the liquid/solid separating 72 to separate the germs from liquid.

Next, the separated germs at the liquid/solid separating 72 is able to go to dewater milling 51 one or more times, so the germ particles are able to be continued recycling back and repeatedly grinding until the germ particle are smaller than screen size opening that is used at liquid/solid separating 72. Next, the heavy phase from germ/fiber separating 52 mix with underflow from oil/protein emulation breaking 56 is sent to fiber/protein separating 25 to produce DDG cake. The liquid from the fiber/protein 25 is sent back to be mixed with grind solid from the dewater milling 51, and the mixture is then sent to germ/fiber separating 52. In some embodiments, the germ/fiber separating process 52 is not included and the ground cake from dewater milling 51 is able to be mixed with the underflow from oil/protein emulsion breaking 56 and to be sent to the fiber/protein separating 25 to produce DDG cake and thin stillage.

The process 60A of the FIG. 6A illustrates some other germ recovering/dewatering process in accordance with some embodiments of the present invention. In the process 60A, the germ/fiber separating 52 is before the liquid/solid separating 72 and the germ is recycled to the front-end. In some other embodiments, the germ is ground at dewater milling 43. In some other embodiments, the germs are ground to break the germs by using a small high shear conic grind milling.

In some embodiments, the inclusion of the back-end grinding milling 51 is able to increase 0.2 lb/Bu of the oil yield. Any screen separating device, such as a pressure screen and a paddle screen, is able to be used at the liquid/solid separating 72. In some embodiments, a disc grinding mill (such as Fluid Quip 36) is able to be used when the dewater milling 51 is followed by germ/fiber separating 52. In some other embodiments, the conic grind mill is able to be used when the germ/fiber separating 52 is followed by dewater milling 51 (not show). Hydrocyclone (germ cyclone) is able to be used at the germ/fiber separating 52 and in conjunction with classification design decanter used at fiber/protein separating 25 for recovering more germs. However, the clarified decanter design is able to be used if recovering more protein with fiber is needed. A multi stage of germ cyclone in series is able to be used when a higher oil yield in needed.

The fiber from the fiber/protein separating 25 of process 60A is able to contain 20% of protein, 8% of oil, and 4% of starch. The fiber is able to be sent to fiber purifying 53 to produce white fiber.

In some embodiments, the ground cake from dewater milling 51 is able to bypass the germ/fiber separating 52 and washing water is added to wash protein, oil and starch off the fiber by using a series of solid/liquid separating process with a counter current setup to produce white fiber. Additional dewater milling is able to be added to the above process.

In some embodiments, the pH is adjusted to be in the range of 7~9 during the fiber purifying 53 to speed up the purification process. In some embodiments, the process 60A is able to generate 1~1.4 lb./Bu of oil, 4 lb./Bu of gluten meal, 2 lb./Bu of spent yeast and germ protein, 1.5 lb./Bu of glycerol, and 0.5 lb./Bu of inorganic salt.

Some of the exemplary results are disclosed below. The process 50 having process of pre-oil/protein separating 55, oil/protein emulsion breaking 56, oil purifying 54, and syrup polishing 57 is able to produce 0.8 lb./Bu of oil and 4 lb./Bu of protein. The process 50A (having the process of back-end germ/fiber separating 52, dewater milling 51, and fiber purifying 53) is able to produce 1.2 lb./Bu of oil (with a less ideal oil quality) in the back-end, 6 lb./Bu of protein (a 50% protein purity), and about 2% alcohol yield increase.

Figure 4:
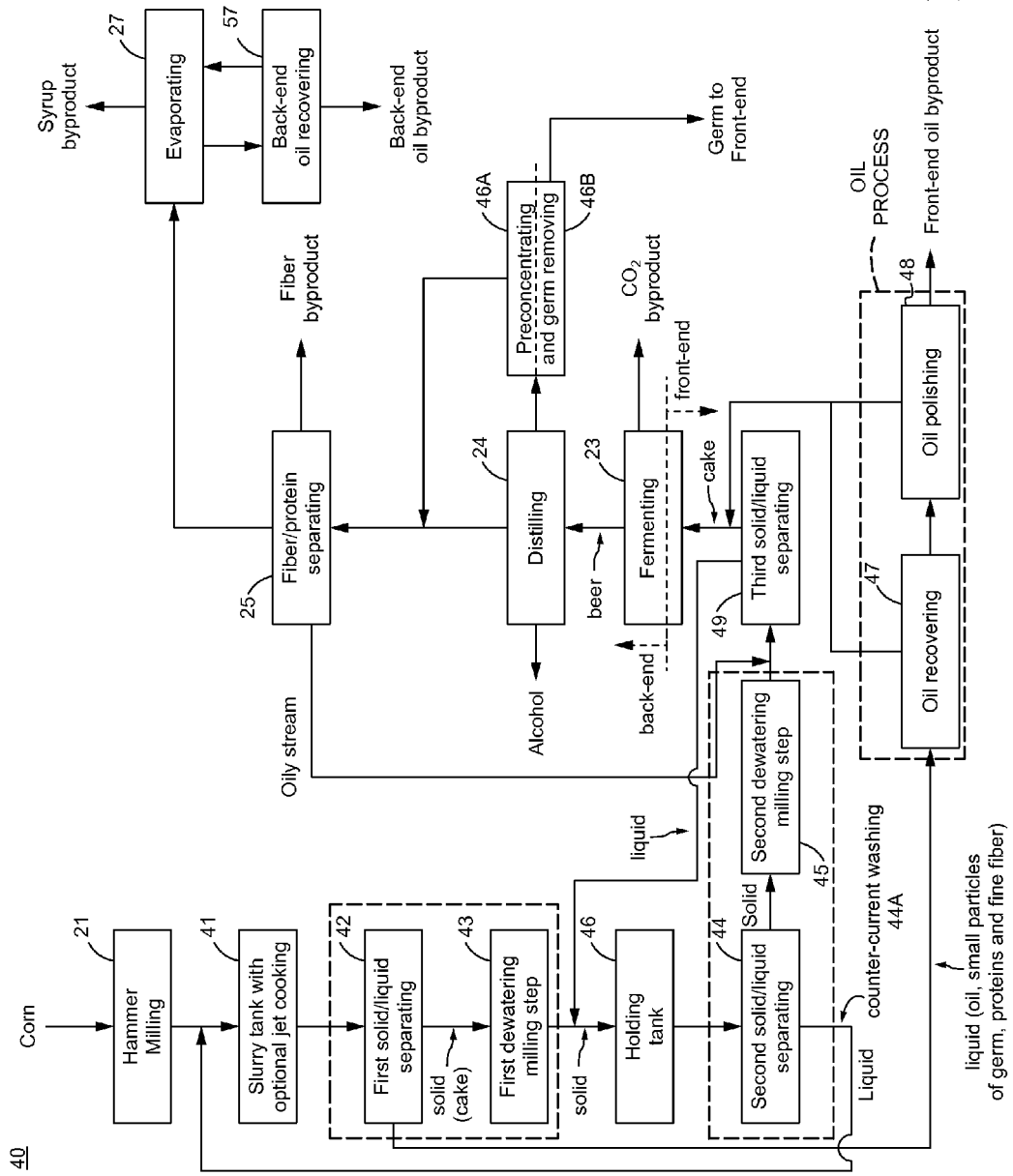
FIGS. 4 and 4A are flow diagrams of dry mill processes with front grinding and front oil recovering in accordance with some embodiments of the present invention.
Figure 4A:
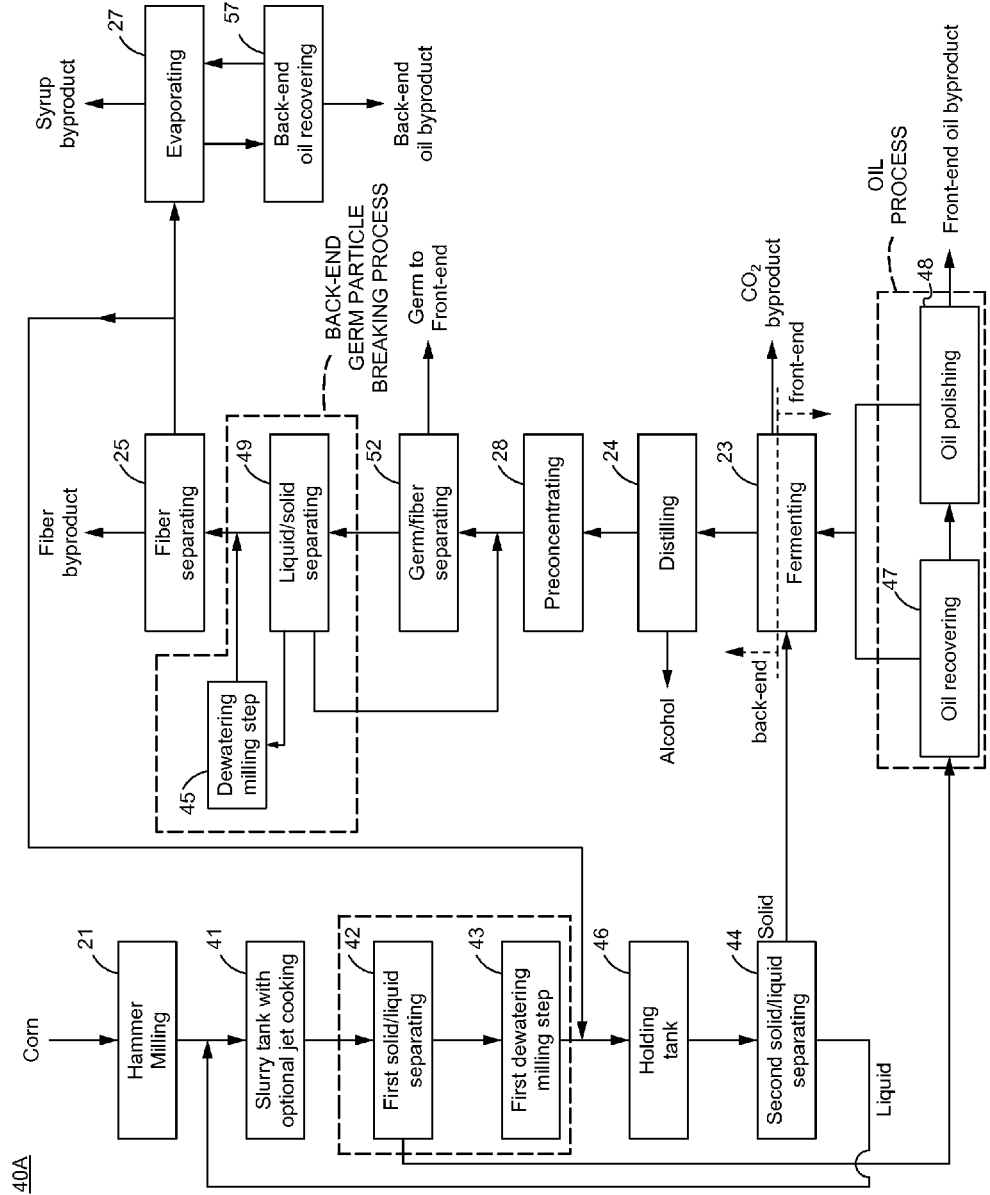

The above described systems/processes, such as 50, 50A, 50B, and 50C, mainly recover oil in the back-end, which produce with less ideal quality oil (dark color and around 13% FFA). The process 40 in FIG. 4 recovers oil in the front-end, which is able to generate oil having a better quality (light color and around 7% FFA). However, the front-end oil recovery system has a lower oil yield (0.5 lb./Bu) that is lower than the oil yield (1.4 lb./Bu oil yield) of the back-end oil recovery system, because in the front-end oil recovery system more than half of oil is still trapped inside the germ and is not able to be released during the liquefaction stage. Most of the oil is released in the fermenting 23 and distilling 24, because the alcohol in the fermenter acts as a solvent that is able to extract oil from the germ particles. Further, high temperature in distilling 24 is able to "cook" the germ, such that oil is able to be released.

In some embodiments, the yield of front-end oil recovery system is able to be increased by recovering oil that is released during the fermenting 23 and distilling 24. The method of increasing the oil yield including a) sending oily stream from the back-end to the front-end and recover oil using the front-end oil system; b) recovering the germs at the back-end and sending the germs back to the front grinds to be ground one more time to release oil and recover oil at the front-end oil recovery system; c) adding the back-end dewater milling 51 to release oil from germs and then sending the oil/protein emulsion back to the front-end to recover oil at the front oil recovery system. More details of the front-end oil recovery system in accordance with some embodiments of the present invention are disclosed below.

The process 60A of FIG. 6A is a front-end oil recovery system in accordance with some embodiments of the present invention. After the jet cooking 41 at the slurry tank, two solid/liquid separating 42 and 44 and dewater milling 43 are performed with a counter current setup 44A, where the corn flour from a hammer milling 21 is mixed with a liquid from solid/liquid separating 44 to a slurry tank 41, such that the grit/germ particles are able to be broken up and the starch is able to be liquefied to release oil from the grits and germs. In some embodiments, cross current washing (e.g., a washing process is added at each stage/process/step) is used instead of counter current washing. In some embodiments, a jet cooker is added to the slurry tank 41. The partial liquefied starch slurry with about 30%~35% of DS from the slurry tank of jet cooking 41 is sent to the first solid/liquid separating 42. The liquid from the first solid/liquid separating 42 that contains most oil with some protein in the liquefied starch solution is sent to an oil recovering 47 (including oil separating) to recover oil as a light phase. The light phase that contains mainly 10%~50% of oil with some oil/emulsion/germ in liquefied starch solution are sent to oil polishing 48 to produce pure oil, which has light color and low fatty acid (around 5%~9% free fatty acid).

The cake/underflow discharge from the oil polishing 48 of process 60A (at an oil polishing centrifuge) containing mainly liquefied starch with solid (protein/fine fiber) are combined with the heavy phase and underflow/cake from the oil separating step 47 to be sent to the fermenter for fermenting 23. The heavy phase discharge from the oil polishing 48 contains an emulsion/germ layer (a combination of oil, germ, protein, and liquefied starch solution with some solid). In some embodiments, the emulsion (normal about 50% oil) in the heavy discharge is further broken up by going through the emulsion breaking 71, such that more oil is able to be recovered. In some embodiments, the breaking of the emulsion is able to be done by using an emulsion breaking technology, such as a) heating to a higher temperature (100° C. to 130° C.), b) adding chemical (emulsion breaker), or c) adding an alcohol.

The oil polishing 48 of the process 60A removes majority of the oil in the light phase and protein solid in the cake phase. The heavy phase contains only emulsion. After running through the oil polishing 48, the volume of the emulsion is decreased to only 10% 30%. This small volume of emulsion is mixed with 200 proof of alcohol to form a solution containing about 20% alcohol, such that the emulsion is able to be broken. Next, the mixture is sent to the fermenter for fermenting 23 and the oil is able to be recovered after distilling 24 either by using a front-end or a back-end oil recovery system.

In some embodiments, a three phase nozzle disc centrifuge and/or other types of disc centrifuge is used at oil recovering 47 of process 60A to separate oil/emulsion layer from the liquefied solution. In some embodiments, the oil polishing 48 is performed using a three phase decanter or a three phase disc centrifuge to separate the pure oil from other substances (emulsion/germ layer and liquefied starch solution).

In some embodiments, the solid phase from the first solid/liquid separating 42 is fed to dewater milling 43 to break up the germ and grit particles, such that the starch is able to be released from grit and oil is released from the germ particles. The grounded solid mixed with cook water form very thick slurry. The slurry is mixed with a fresh enzyme to lower the brix (around 15 to 20 Brix) of the slurry in multiple holding tanks (e.g., 2 or 3) for about 3 to 6 hours at a predetermined liquefied temperature (around 180° F.). Next, the slurry is sent to solid/liquid separating 44 to separate the liquid from solid. The liquid contains 15 to 20 Brix of liquid starch solution with some oil and protein, which is sent to a slurry tank as cook water.

The solid from solid/liquid separating 44 is mixed with the heavy phase and underflow/cake phase discharge from oil recovering 47 and oil polishing 48 to be sent to the fermenter at fermenting 23. In some embodiments, a paddle screen (and other dewatering devices such as pressure screens and vibration screens) is used for the solid/liquid separating 42 and 44. In the dewatering milling 43, the grit and germ particles are broken up to smaller particles without breaking up fiber. In some embodiments, the grinding uses a disc grinding mill at the dewater milling 43. A person of ordinary skill in the art appreciate that other grinding mills are applicable, such as pin mills. The starch in the grits and germs are able to be exposed to an enzyme and are liquefied before sending them to the fermenter at the fermenting 23. The one dewater milling stage with a counter current washing set up in process 60A FIG. 6A is disclosed as an example. A person of ordinary skill in the art appreciate that the front oil recovery system is able to have two or three grinding milling stages in series with and/or without a counter current set up.

In some embodiments, one dewater milling is used to cut the germ particles to about half of their sizes. For example, an 1 mm germ particle is able to be reduced to about 500 to 600 micron after going through one stage of the dewater mill. In some embodiments, a two or three stage dewater milling in series is used to reduce the germ particles to smaller sizes and to extract more oil, such that a higher oil yield is able to be obtained. Although having multiple dewater milling is able to have a higher oil yield, the costs associated are also higher.

In accordance with some embodiments, there are at least two ways to reduce the number of milling stage: a) setting up a counter current wash to recycle the middle size germ particles back to the front dewatering mill; and b) adding the de-germ system in the front-end or back-end to recycle the germ particles to the front milling stage. The amount of oil that is released in the front-end mill is able to be affected by a) particle size, b) holding time in the liquefaction, c) the liquefaction conditions, temperature, type and amount of the enzyme used, and Brix. With the above disclosed processes, oil is released and extracted in the fermentation. Further, the yield of oil in the fermentation process is able to be affected by a) type of enzyme and amount, b) condition of the fermenter, such as temperature, amount/percentage of the alcohol, and holding time, and c) particle sizes. Accordingly, by optimizing the above condition, oil yield is able to be increased.

After fermenting, distilling, and fiber separating, the fiber is able to contain 9% 11% of oil without going through any front mills, 6% to 9% of oil when one grinding mill is used, 3% to 6% of oil when two grinding mills are used in series, and 1% to 3% of oil when three grinding mills are used in series. The lower amount of oil in the fiber reduces the oil loss, such that the oil yield is increased.

After fermenting 23 and distilling 24, the bottom layer of the distillation (whole stillage) contains fiber and germ particles, corn proteins, yeasts, and byproducts from fermenter and ash from corn. The whole stillage still has about 0.5 to 2.5 lbs./Bu of germs and 4 to 5 lbs./Bu fiber. Both solids have the same particle sizes range from less than 50 micron up to more than 1 mm.

The germ particles in the front-end that do not fully absorb water are much harder and tough to be broken up by using a grinding mill. The germ particles, after fermenting and cooking at the bottom of a distillation device, fully absorb water and are much softer to be broken by grinding mills. Accordingly in some embodiments, the combination of germ cyclone and classification decanter are used to separate the germs from fiber at the back-end after distilling and the germs are recycled back to the dewater milling 43 in the front-end or germ milling 73 in the back end. In some embodiments, two dewater milling are used (but not used in series in the front end) including one in the front-end (first dewater milling 43) for increasing an alcohol yield and other one in back-end (germ milling 73) for increasing an oil yield.

In the process 60A of FIG. 6A, the whole stillage from distilling 24 goes to preconcentrating 28 to increase the solid concentration from 12%~14% of DS to 15%~25% of DS by using a first evaporator. Next, the whole stillage is mixed with the overflow from the fiber/protein separating 25 and is sent to the germ/fiber separating 52 to separate the germ particles from fiber by using density differences. In the germ/fiber separating 52, the germ particles (density around 1) is lighter than fiber (density around 1.15), so the germ particles are able to be in the overflow stream from top of the cyclone and the fiber is in the underflow stream from the bottom of cyclone.

In some embodiments, the overflow from germ/fiber separating 52 of process 60A is sent to a liquid/solid separating 72 to recovery germ particles. Next, the germ particles are sent to dewater milling 43 in the front-end to further break down to smaller particles until the particles are smaller than the screen open size on liquid/solid separating 42. In some embodiments, the separated germs are sent to a high shear grinding mill, such as the conic grinding milling 73, before the germs are sent back to the front-end for oil recovery in the front-end.

In some embodiments, the underflow from germ/fiber separating 52 is mixed with the underflow from oil/protein emulsion breaking 56 and goes to the fiber/protein separating 25 to produce DDG. In some embodiments, the washing water 25A is added to the fiber/protein separating 25 to wash protein off the fiber. Next, the de-protein fiber is sent to a fiber purifying 53 to produce white fiber as a raw material for secondary alcohol production or paper industry. In some embodiment, the fiber purifying 53 is not performed and the de-protein fiber is used to produce DDGS. The washing liquid with protein and starch from the fiber purifying 53 is able to be recycled back to the front-end as part of the cook water.

An oil recovery system with the back-end grinding milling, such as dewater milling 51, is able to increase the oil yield about 0.2 lb/Bu. In some embodiments, the solid/liquid separating 72 uses a screen type device, such as paddle screen and pressure screen. In some embodiments, the fiber/protein separating 25 uses a decanter, a fiber centrifuge, a paddle screen follow by a press, or a combination thereof to remove/recover protein from the fiber. The filtrations, such as fiber centrifuge, are able to separate the germs from fiber by the sizes of the particles and perform the counter current washing of the fibers to recover more protein. Similarly, the decanters are able to perform classification and separate germs from fibers by density.

The cake (fiber portion) from the centrifuge at the liquid/solid separating 72 forms a DDGS byproduct. The liquid from the solid/liquid separating 72 is mainly de-fiber protein solution, which is different from a thin stillage from a decanter of a typical dry milling process. The de-fiber protein solution from the solid/liquid separating 72 in process 60A of FIG. 6A contains more than 70% of protein in the whole stillage, which has a much higher protein percentage when compared with the thin stillage from a decanter of a typical dry mill plant (e.g., only 20 to 30% of protein in the whole stillage).

In some embodiments, the de-fiber protein and oil slurry from the solid/liquid separating 72 is sent to pre-oil/protein separating 55, such that the oil/protein slurry is able to be separated into two streams. One of the streams is an oil rich stream and the other stream is a protein rich stream. The oil/protein slurry is able to contain about 2% insoluble protein and 1% oil, which is able to be separated to two layers using a simple holding tank with several hour of holding time. One of the two layers includes the light layer, which is an oil rich stream containing more oil (around 1.3% to 1.7% of oil) and less protein (1.3% to 1.7%) on top of the settle tank. The other layer is a heavy layer, which is a protein rich stream containing less oil (0.3% to 0.7%) and more protein (2.3% to 2.7%) at the bottom of settle tank. In some embodiments, the heavy layer (protein rich stream) from pre-oil/protein separating 55 is sent to oil/protein emulsion breaking 56. The light layer (oil rich stream) from the oil/protein separating 55 is sent to the front-end as a back-set, which is used as part of the cook water. The heavy phase from the oil/protein emulsion breaking 56 is sent to an evaporator for evaporating 27 with an option of being sent to protein dewatering 32 to produce a protein cake. Next, the overflow from the protein dewatering 32 is sent to the evaporator for evaporating 27.

In some embodiments, three phase centrifuges (such as decanter types to produce dry cake) are used in the oil/protein emulsion breaking 56. The cake phase from the three phase decanter or disc decanter is able to produce a protein cake without the protein dewatering 32. In some other embodiments, three phase disc centrifuges are used. The underflow/sludge phase is able to produce wet cake by using protein dewatering 32 or making the underflow back to fiber/protein separating 25. In some embodiments, the light phase from the oil/protein emulsion breaking 56 is sent to the front-end, such that the oil is able to be recovered by using a front-end oil recovery system (e.g., oil recovering 47 and oil polishing 48). In some embodiments, oil purifying is able to be added, such as the oil purifying 54 is added after oil/protein breaking step 56 as show in process 50A of FIG. 5A.

In some embodiments, a large thin stillage holding tank is used and more than four hour holding time is used for the oil/protein separating 55. In some embodiments, an incline plate settler is used to increase a separation area with smaller holding/settle tank. In some embodiments, gas (air or $CO_2$) in the form of fine bubble is added to speed up the oil/protein separating 55. In some other embodiments, coagulated agent and commercial air floatation unit are used.

In some embodiments, the oil/protein emulsion breaking 56 uses high speed centrifuges, such as two or three phase nozzle centrifuge, to break the bonds between the oil and protein by density different (oil is 0.9 gram/ml and protein is 1.15 gram/ml). In the oil/protein emulsion breaking 56, the light phase stream (with about 10%~30% of liquid) contains mainly oil, oil/emulsion, and fine germ particles. The heavy phase stream (with about 50%~80% of liquid) contains mainly proteins and fine fibers and sometimes with germ particles depending on the size of the germs and the density of the liquid. The underflow/cake phase stream contains mainly gluten meal (5%~10%). The light phase from the oil/protein emulsion breaking 56 contains about 3%~6% oil, which is sent back to the front-end as a back-set fluid. In some embodiments, oil purifying 54 is added to produce pure oil in the back-end as show in process 50A in FIG. 5A

In some embodiments, the heavy phase discharged from oil/protein emulsion breaking 56 is sent to an evaporator for evaporating 27. The underflow/cake phase from the three phase centrifuges contain mainly corn gluten with some germ and spend yeast. The amount of germ and spent yeast in the underflow/cake phase is variable/controllable depending via controlling the three phase centrifuge operation conditions.

In some embodiments, three phase decanters or three phase disc decanters are used in the oil/protein emulsion breaking 56. The cake phase from the three phase decanters is able to be sent to a dryer at protein dewatering 32 to produce protein meal (having 50% protein and less than 3% of oil). In some embodiments, the cake phase is mixed with DDGS to be a part of DDGS byproducts.

In other embodiments, three phase disc centrifuges (Desludger or nozzle centrifuge) are used on in the oil/protein emulsion breaking 56. The underflow from the three phase disc centrifuge is able to contain soapy cake. In some embodiments, protein dewatering 32 and/or fiber protein separating 25 is used for further dewatering the soapy cake before sending the cake to a dryer.

In some embodiments, the heavy phase discharge from oil/protein emulsion breaking 56 and overflow from the protein dewatering 32 are sent to an evaporator for evaporating 27 to be concentrated to have 20%~40% of total solid before the heavy phase is sent to syrup polishing 57.

The light phase stream from the syrup polishing 57 contains mainly emulsion and fine germ particles with a high oil content (more 30% of oil), which is able to go through various emulsion breaking processes, such as heat, chemical, or added alcohol to break the emulsion and recover more oil. In some embodiments, the emulsion is sent to a DDGS dryer to become part of the DDGS.

The heavy liquid stream from the syrup polishing 57 that contains mainly soluble solid from corn and fermenting byproducts, such as glycerin, is sent to the evaporator for evaporating 27 to be concentrated to about 50%~80% of DS and produce syrup as a byproduct. The underflow/cake flow from the syrup polishing 57 contains mainly germ protein and spent yeast, which is able to be mixed with a protein cake (mainly gluten) from the protein dewatering 32. In some embodiments, the underflow/cake is able to be used to produce high value protein meal for fish. In some other embodiments, the underflow/cake is sent to be mixed with the fiber cake received from fiber separating 25 to produce a DDGS byproduct.

In some embodiments, the syrup polishing 57 is used between multi-stage evaporating to separate the small germ particles (with more than 30% of oil) from spent yeast and germ protein. The concentrated syrup (with a higher density) floats the lighter germ particle (because with oil) to the top to be together with the oil/emulsion layer and not sinks to the bottom (having the spent yeast and germ protein (heavier because low oil content)).

The dry milling in accordance with some embodiments is able to contain three to six evaporators in series. The syrup generated by the dry mill is able to have a concentration from around 4% of DS to 40% of DS or higher. In some embodiments, the syrup polishing 57 is operated with 20% of DS syrup as a feed, which generates a higher protein yield with higher oil content in the protein cake resulting in a lower oil yield. In some other embodiments, the syrup polishing 57 is operated with 40% of DS syrup as a feed, which generates lower yield of protein with lower oil content in the protein cake resulting in a higher oil yield. In some embodiments, the de-oil and de-protein syrup is further concentrated to having up to 80% of DS without create evaporator fouling problem. The high concentrated de-oil and de-protein syrup is able to further be sent to glycerol separating 58 and inorganic salt separating 59 to recover high value glycerin and inorganic salt.

The process 60A of FIG. 6A is directed toward a dry mill process with a front-end oil recovery system in accordance with some embodiments of the present invention. The process 60A includes four advantageous features. These four features are able to be selectively added to a typical dry mill process to produce a high quality and quantity valuable byproducts. The four features include the fiber purifying 53, germ/fiber separating 52, solid/liquid separating 72, and germ milling 73. In the case when the white fiber production is not needed while want to have more than 6% of oil in the DDGS, the process 60 of FIG. 6 is able to be used.

Some exemplary results are disclosed in the following. In some embodiments, the process 60A is able to generate 1.4 lb./Bu of oil, 6 lb./Bu of protein meal, 1.5 lb./Bu of glycerin, 0.5 lb./Bu of inorganic salt, 2.5 lb./Bu of syrup and 3. lb./Bu of white fiber, and 3% of alcohol yield increase. In some embodiments, the process 60A without the fiber purifying 53 is able to generate 1.2 lb./Bu of oil, 5.5 lb./Bu of protein meal, 1.5 lb./Bu of glycerin, 0.5 lb./Bu of inorganic salt, 6.2 lb./Bu of DDGS, and 3% of alcohol yield increase. In some embodiments, the process 60A without glycerin separating 58 and inorganic salt separating 59 is able to generate 1.2 lb./Bu of oil, 5.5 lb./Bu of protein meal, 8.2 lb./Bu of DDGS, and 3% of alcohol yield increase. In some embodiments, the process 60A without germ/fiber separating 52, solid/liquid separating 72 and germ milling 73 is able to generate 1.0 lb./Bu of oil, 4.5 lb./Bu of protein meal, 9.6 lb./Bu of DDGS, and 2% alcohol yield increase. In some embodiments, the process 60A without syrup polishing 57 is able to generate 0.8 lb./Bu of oil, 3.5 lb./Bu of protein meal, 10.8 lb./Bu of DDGS, and 2% of alcohol yield increase. In some embodiments, the process 60A without oil/protein emulsion breaking 56 (with front-end grinding and front-end oil recovery system) is able to generate 0.5 lb./Bu of oil, 15.1 lb./Bu of DDGS, and 2% of alcohol yield increase. In some embodiments, the process 60A without protein recovering 66 and protein dewatering 32 is able to generate 0.5 lb./Bu of oil, 14.6 lb./Bu of DDGS, and 2% of alcohol yield increase. In some embodiments, the process 60A without the front-end grinding and without the front oil recovery system is able to generate 15.6 lb./Bu of DDGS.

Figure 7:
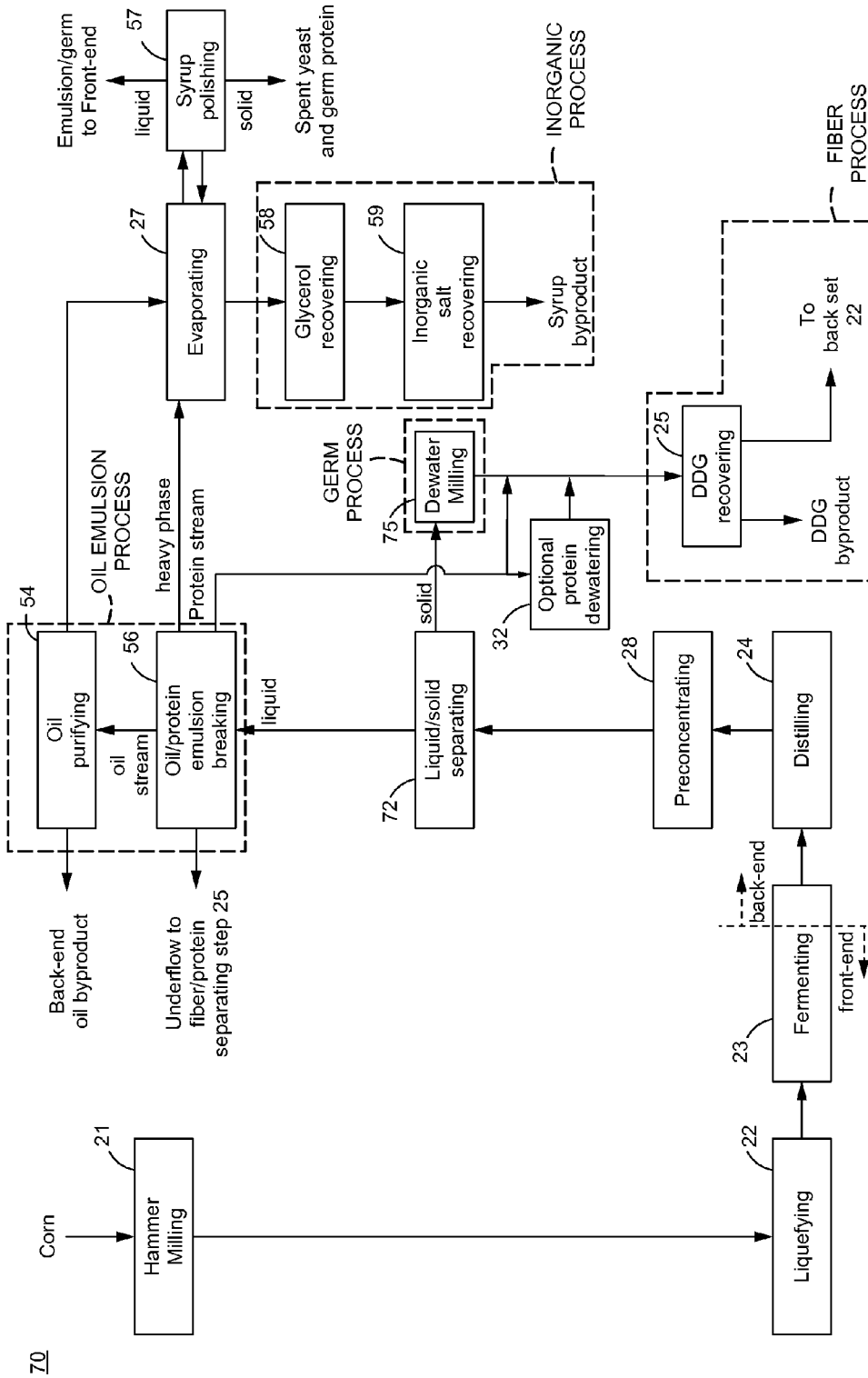
FIGS. 7 and 7A are flow diagrams of dry milling processes with back end oil recovering and back end milling in accordance with some embodiments of the present invention.

The process 70 of FIG. 7 illustrates a back-end oil recovery system with back-end grinding in accordance with some embodiments of the present invention. In the process 70, the germ particles that go through fermenting 23 and distilling 24 are able to fully absorb water and become much easier to be broken up and to release oil at the dewater milling 75 at the back-end.

The process 70 includes hammer milling 21, liquefying 22, fermenting 23, distilling 24, preconcentrating 28, and solid/liquid separating 72, which are processes that are also included in the process 50 of FIG. 5.

The solid phase from liquid/solid separating 72 contains mainly larger solid particle, such as fiber, germ, and hard endosperm, which is sent to dewater milling 75 to break up the germ and grit particles and to lease oil and starch. The liquid phase from liquid/solid separating 72 contains mainly fine fiber, protein solid and all soluble solid inside the corn. The liquid is sent to oil/protein emulsion breaking 56 to be separated into a light phase (oil rich stream), a heavy phase (low oil and protein stream), and an underflow stream (the highly concentrated protein stream) on a three phase nozzle centrifuge (or other types of three phase separation centrifuges). In some embodiments, the underflow of the oil/protein emulsion breaking 56 is sent to the protein dewatering 32 to recover protein before mixing with the solid phase from the dewater milling 75. Next the mixture is sent to DDG recovering 25 to recover fiber and protein mixture as a solid phase (a DDG byproduct). The liquid from DDG recovering 25 that contains germs, germ protein and fine protein solid is sent back to the front-end as part of the back-set fluid.

The light phase from the oil/protein emulsion breaking 56 is sent to oil purifying 54 to recover oil in the back-end. The heavy phase from the oil purifying 54 and oil/protein emulsion breaking 56, which contain less oil and protein, is sent to an evaporator in the evaporating 27. Next, syrup polishing 57 is performed to recover emulsion layer as a light phase and germ/yeast protein layer as the solid phase, which is similar to the process described in the process 50 of FIG. 5. In some embodiments, the concentrated syrup is sent to glycerol recovering 58 and inorganic salt recovering 59, which is similar to the process described in the process 50 of FIG. 5.

Figure 7A:
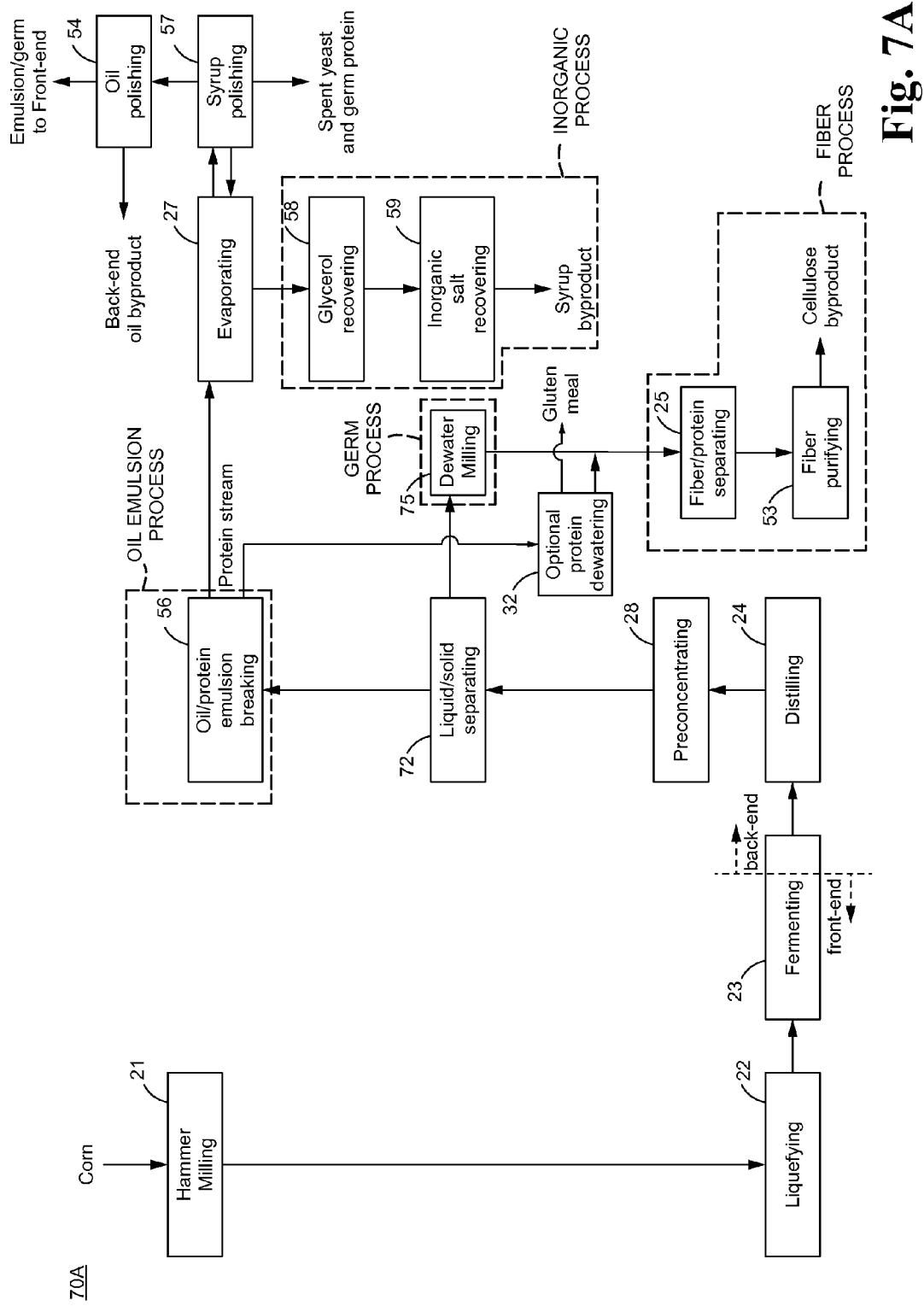

In some embodiments, the process 70 of FIG. 7 contains a three phase nozzle centrifuge, which is used at the oil/protein emulsion breaking 56. In some other embodiments, the process 70A of FIG. 7A includes a two phase nozzle centrifuge, which is used at the oil/protein emulsion breaking 56. In the process 70A, the light phase (oily rich stream) is combined with the heavy phase (low oil and protein stream) of the oil/protein emulsion breaking 56 and are sent to the evaporator for evaporating 27 to concentrate the solution to contain 20%-30% of DS.

Next, the syrup polishing 57 is used to recover germ/yeast protein in the solid phase, oil/emulsion/germ paste in the light phase, and clean syrup (oil and protein free) in the heavy phase. The clean syrup is able to be further concentrated to as high as 80% of DS. In some embodiments, the clean syrup is sent to glycerol recovering 58 and inorganic salt recovering 59. The light phase of the syrup polishing 57, including the oil/emulsion/germ paste, is sent to front end as part of a back-set flow. In some embodiments, the germ paste is further treated for emulsion breaking/extracting (such as added alcohol), such that more oil is able to be recovered.

The underflow stream from the oil/protein emulsion breaking 56, containing mainly protein stream, is sent to protein dewatering 32 to recover the protein meal. The overflow from the protein dewatering 32 is mixed with the ground cake from the dewater milling 75 and is sent to a decanter (of the fiber protein separating 25) to separate the fiber (DDG). In some embodiment, the fiber is further purified in the fiber purifying 53 after the dewater milling 75 and counter current washing with optional caustic treatments (such as, pH 7~9) depend the fiber purity wanted.

In some embodiments, the oil/protein emulsion breaking 56 in the processes 50, 50A, 60, and 60A use high speed nozzle centrifuges to break down the bonds between oil and protein (with some fine fiber) and separate the solution into two streams including one oil rich stream and the other protein rich stream. The "free oil" in the oil rich stream (from the oil/protein emulsion in a high speed centrifuge) is able to be recovered by using either the front-end recovering system (such as the oil recovering 47 and oil polishing 48 of process 60A of FIG. 6A) or the back-end oil purifying 54 (such as process 70 of FIG. 7). In some embodiments, the protein rich stream produces high protein meal (more than 50% protein) by further going though protein dewatering 32.

The differences among the exemplary processes include that the light phase (oil rich stream) of the processes 50 and 50A from the pre-oil/protein separating 55 is fed to oil/protein emulsion breaking 56. In the processes 60 and 60A, the heavy phase from pre-oil/protein separating 55 is fed to oil/protein emulsion breaking 56.

By having pre-oil/protein separating 55, oil/protein emulsion breaking 56, syrup polishing 57, glycerin separating 58, inorganic separating 59, back-end dewater milling 51, and fiber purifying 53 in some embodiments of the present invention, valuable byproducts, such as oil, proteins (gluten, spent yeast and germ protein), white fiber and glycerol and organic plant food are able to be generated. A person of ordinary skill in the art appreciates that the above processes and systems are able to be selectively/optionally combined in any way and in any order.

Figure 8:
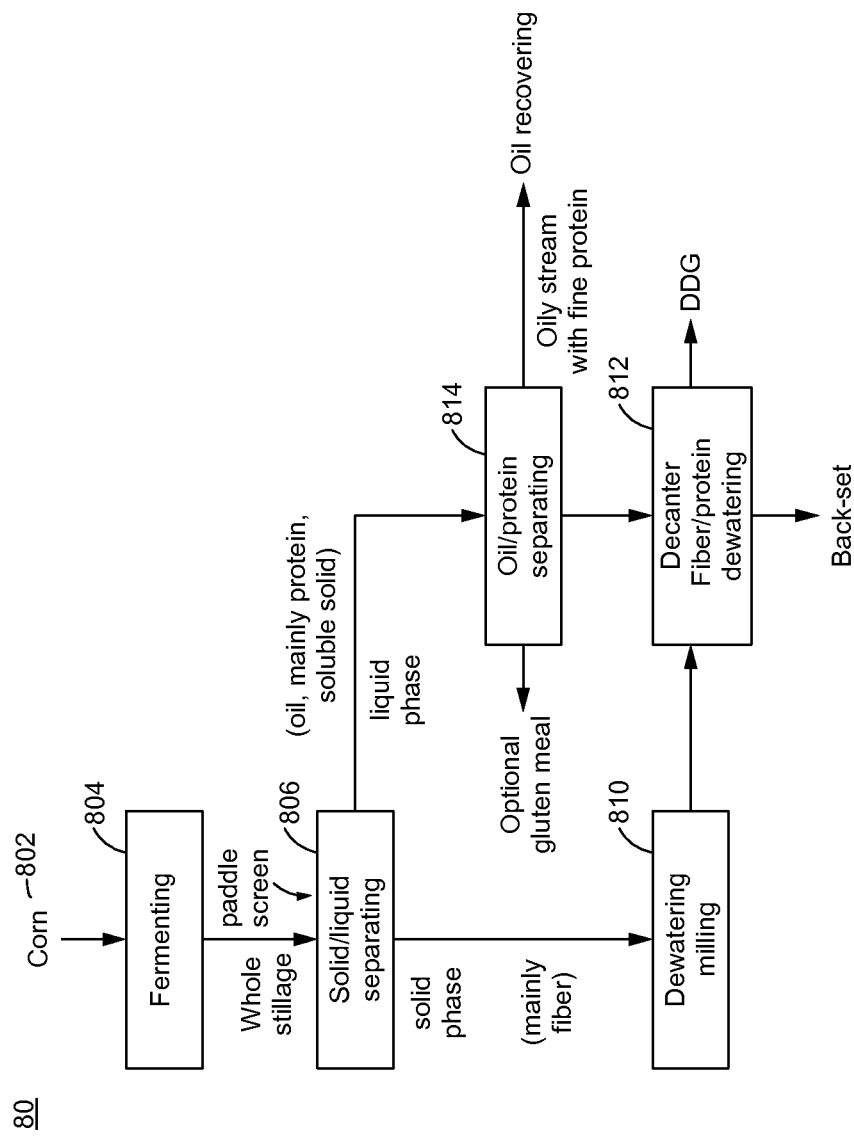
FIGS. 8 and 8A are flow diagrams of dry milling processes with back-end milling and back-end oil recovery processes in accordance with some embodiments of the present invention.
Figure 8A:
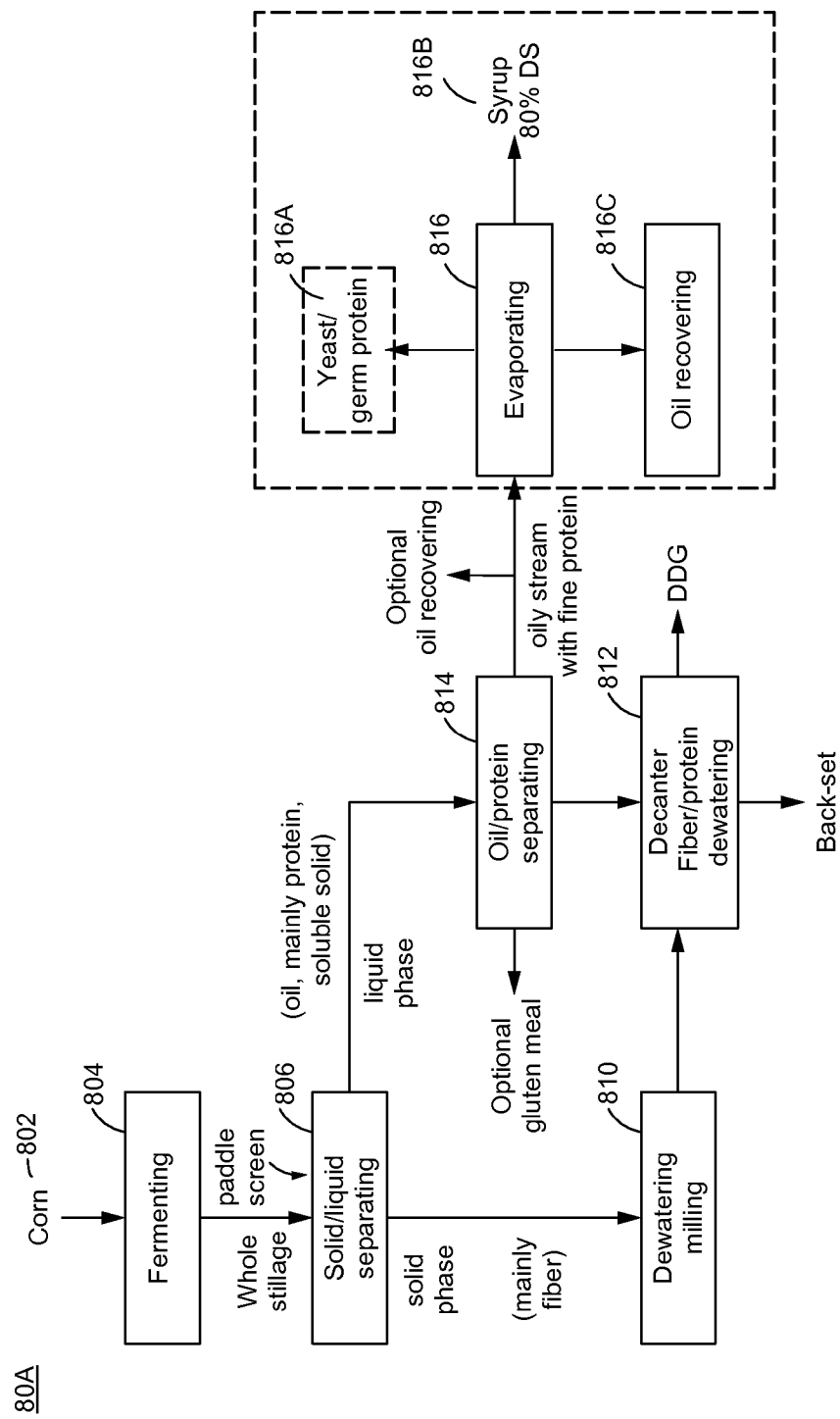

FIGS. 8 and 8A are flow diagrams of dry milling system with back-end milling and back-end oil recovery processes 80 and 80A in accordance with some embodiments of the present invention.

In FIG. 8, the whole stillage, after fermenting 804, is sent to solid/liquid separating 806. Optional intermediate processes from corn preparing 802 via the fermenting 804 to the solid/liquid separating 806 are not further described here for succinctness. In some embodiments, the solid/liquid separating 806 uses a paddle screen. The solid phase (containing mainly fibers) from the solid/liquid separating 806 is sent to dewater milling 810. The liquid phase (containing mainly protein, oil and soluble solid) is sent to oil/protein separating 814.

In the dewater milling 810, the germs are ground such that oil is able to be released from the germs. Advantageously, the process/system with the dewater milling 810 is able to produce more oil than the systems of the typical dry mills, because the germs particles in the process 80 of the present invention fully absorb water in and before the fermenting 804. The corn kernel becomes soft and easy to break after the fermenting 804, so more oil and germs are able to be release out from the kernel. In some embodiments, the oil released is sent to the processes/devices for oil recovery in the back-end.

In some embodiments, the ground mixture from the dewater milling 810 is sent to the fiber/protein dewatering 812. In some embodiments, a decanter is used at the fiber/protein dewatering 812. In some embodiments, the solid from the fiber/protein dewatering 812 is sent to produce DDG. The liquid from the fiber/protein dewatering 812 is able to be used as a back-set stream for the process/step that needs to add water.

In the oil/protein separating 814, protein stream (gluten protein) is able to be sent to the fiber/protein dewatering 812. In some embodiments, gluten produced at the oil/protein separating 814 is sent to make gluten meal. The oily stream from the oil/protein (containing oil and fine protein) is sent to a back-end oil recovery device for oil recovery. Advantageously, the process 80 described above is able to recover oil in the back-end process without using any evaporator or evaporating steps. In some embodiments, the process 80 recovers oil without condensing/evaporate the oily stream to form syrup from the oil/protein separating 814. In some embodiments, the oil/protein separating 814 uses a two-three phase nozzle centrifuge.

The process 80A of FIG. 8A is similar to the process of 80. The process 80A is able to include the processes/steps in the process 80. Additionally, the oily steam from the oil/protein separating 814 is able to be sent to an evaporator for evaporating 816. In the evaporating 816, one part of the output contains yeast/germ protein 816A, another part is able to be used for oil recovery 816C, and another part of the output contains highly concentrated syrup 816B (such as having 80% of DS), which is able to be processed to recover glycerol and inorganic salt.

Figure 9:
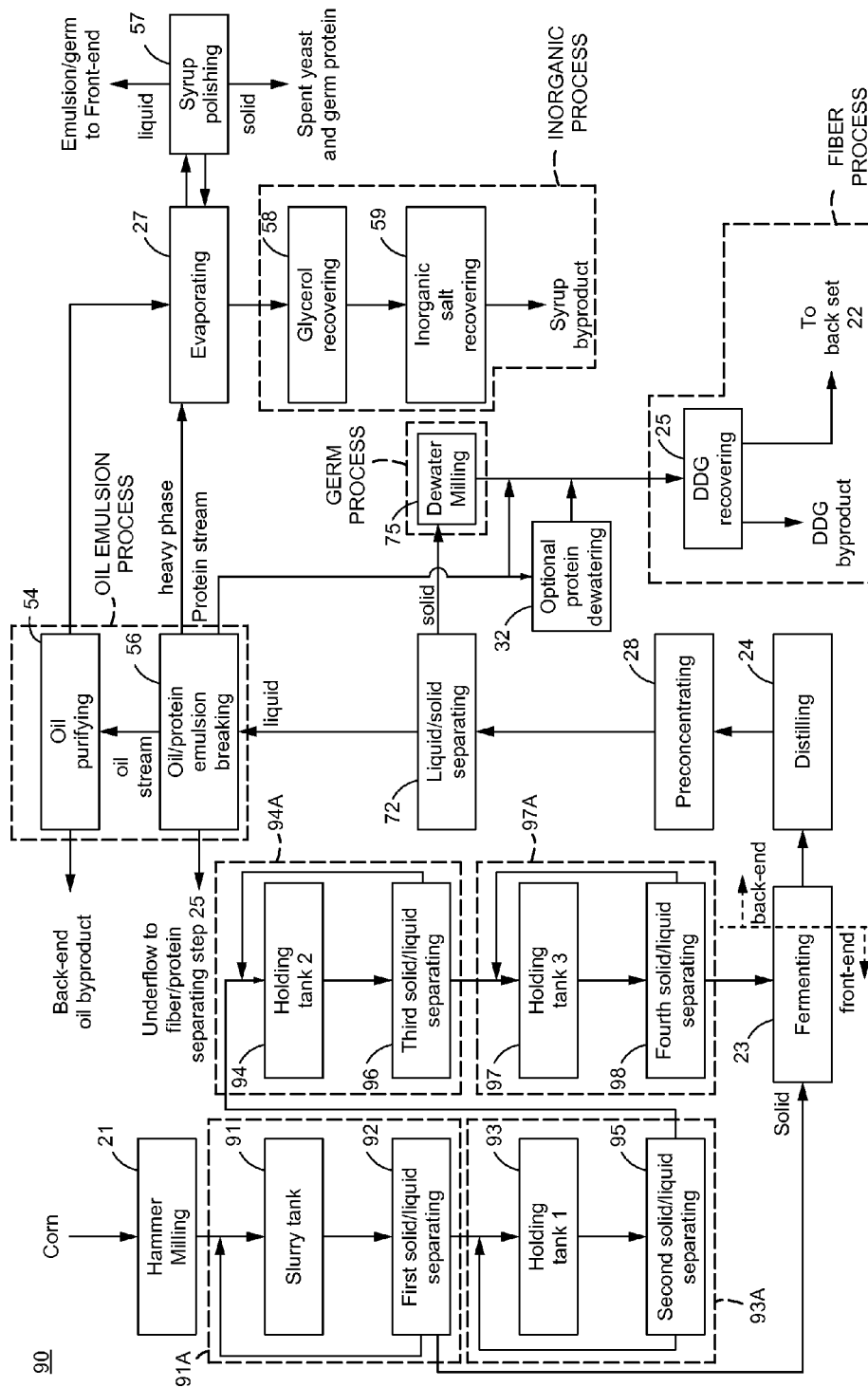
FIGS. 9 and 9A are flow diagrams of dry milling processes with multiple counter current washing in accordance with some embodiments of the present invention.

FIG. 9 illustrates a dry milling process with multiple counter current washing 90 in accordance with some embodiments of the present invention.

The process 90 of FIG. 9 includes a four stage counter current washing 91A, 94A, 93A and 97A in the front end. Each of the counter current washing setup is able to lower the degree of Brix to a pre-determined degree. The first counter current washing setup 91A includes receiving ground corns from hammer milling 21 at a slurry tank 91. The output from the slurry tank 91 is sent to the first solid/liquid separating 92 to separate the solid from the liquid. The solid portion is sent to fermenting 23 at a fementor. The liquid portion from the first solid/liquid separating 92 is split into two streams. One of the streams from the first solid/liquid separating 92 is sent back to the slurry tank 91 forming the first counter current washing. The other stream from the first solid/liquid separating is sent to a first holding tank 93. The first holding tank 93 and the second solid/liquid separating 95 form the second counter current washing 93A.

In the second counter current washing 93A, the liquid from the second solid/liquid separating 95 is sent back to the first holding tank 93 to form a stream of counter current washing. The solid from the solid-liquid separating 93A is sent to the second holding tank 94.

In the third counter current washing 94A, the content in the second holding tank 94 is sent to the third solid/liquid separating 96 after a predetermined period, such as 4 hours. The solid portion from the solid/liquid separating 96 is sent to a third holding tank 97 and the liquid portion is sent back to the second holding tank 94 as a stream of counter current washing.

In the third counter current washing 97A, the third holding tank 97 receives solid from the third solid/liquid separating 96. The content in the third holding tank 97 is mixed with a stream of cook water. The mixture is sent to fourth solid/liquid separating 98. The liquid from the solid/liquid separating 98 is sent back to the third holding tank 97 as a stream of counter current washing. The solid from the fourth solid/liquid separating 98 is sent to fermenting 23.

With the multiple stages of the counter current washing, the degree of brix on three holding tank is able to be 15~20 Brix at the first holding tank, 7~15 Brix at the second holding tank, and 2~6 Brix at the third holding tank. The counter current washing setup at the liquefaction stage with a lower brix is able to avoid the formation of the un-fermentable starch and increase the liquefaction efficiency, such that the liquefaction time is able to be shortened. The counter current washing is also able to be divided into three liquefaction zones, such that different types of enzymes, a different amount of the enzymes, and different liquefying conditions (such as, temperature and pH) are able to be applied at the different liquefying zones to have an optimized result.

The counter current washing set up is also able to be used to increase the solid holding time inside the three holding tanks. The numbers of the stages of the counter current washing are able to vary. The back end processes of the process 90 in FIG. 9 are able to be the same as process 70 of FIG. 7 or 70A of FIG. 7A.

Figure 9A:
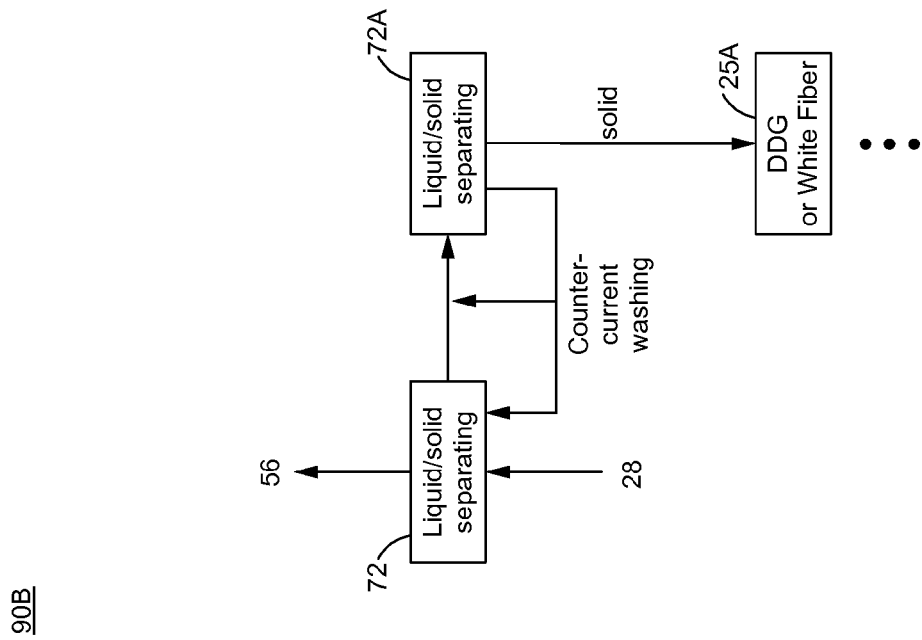
Figure 9A:
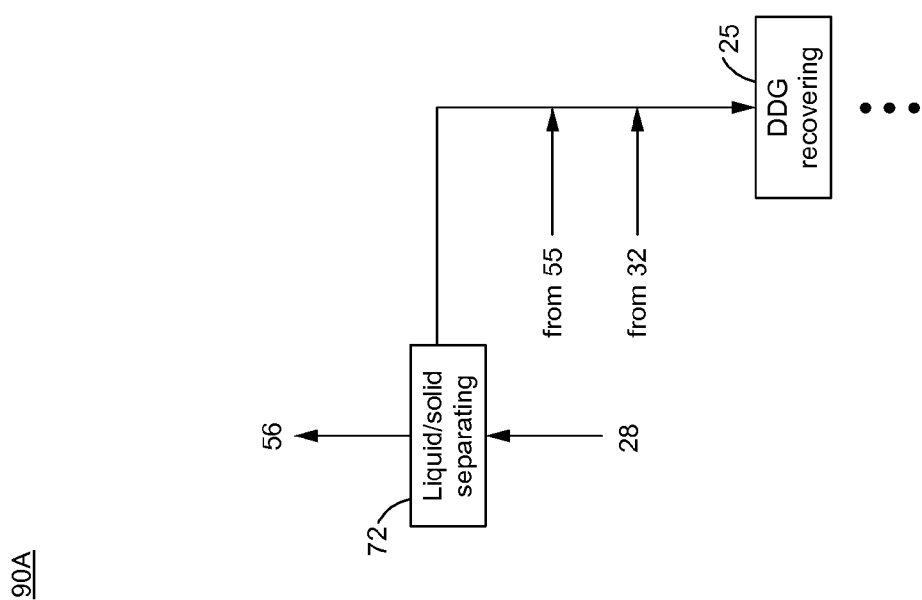

FIG. 9A illustrate processes 90A and 90B, which are derivative processes of the process 90 of FIG. 9. The process 90A illustrates a process without using the dewater milling 75. The solid from the liquid/solid separating 72 is sent to the DDG recovering 25 without using the dewater milling 75 of FIG. 9. The process 90B illustrates another process using multiple liquid/solid separating process to replace the dewater milling 75. The solid from the liquid/solid separating 72 is sent to another liquid/solid separating 72A. The liquid from the liquid/solid separating 72A is able to be sent back to 72 or 72A as a stream of counter current washing. The solid from the liquid/solid separating 72A is able to be sent to DDG or white fiber recovering 25A. Multiple liquid/solid separating 25A is able to be used, such as 1, 2, 5, and 10, depending on the purity of the white fiber that is pre-determined.

Generally throughout the present disclosure, the processes/steps that are before the fermenting 23 are part of the front-end process and the processes/steps that are after the fermenting 23 is part of the back-end process. While the present invention has been illustrated by a description of various embodiments and while these embodiments have been described in considerable detail, it is not the intention of the applicant to restrict or in any way limit the scope of the appended claims to such detail. For example, although the various systems and methods described herein have focused on corn, virtually any types of grains, including, but not limited to, wheat, barley, sorghum, rye, rice, oats and the like, are able to be used. The embodiments of the present invention is able to be used to produce white fiber for paper industry and used as a feed stock for secondary alcohol production, clean sugar solution for butanol, lysine and plastic production.

In utilization, the methods and devices disclosed herein are able to improve oil yield and recover valuable byproducts from corns. In operation, fiber process, germ process, inorganic salt and glycerol recovery process, and oil emulsion process are able to be used either before or after the fermenting. Advantageously, the methods of and devices disclosed herein are able to produce high quality corn oil and pure byproducts from corns.

Thus, the invention in its broader aspects is therefore not limited to the specific details, representative apparatus and method, and illustrative example shown and described. Accordingly, departures is able to be made from such details without departing from the spirit or scope of applicant's general inventive concept.

What is claimed is:

1. A method of producing oil using a dry milling system comprising:
   a) separating a whole stillage into a solid portion and a liquid portion after fermenting; and
   b) grinding the solid portion after the separating to release a first oil from germs and release the starch from grit in kernels of grains; and
   c) separating a second oil and protein in the liquid portion.

2. The method of claim 1, wherein the grinding comprises dewater milling.

3. The method of claim 2, wherein the first oil is recovered at oil recovering after fermenting.

4. The method of claim 1, wherein the liquid portion contains the protein, the second oil and a soluble solid.

5. The method of claim 1, wherein the separating the second oil and the protein separates the liquid portion into an oily part and a protein part.

6. The method of claim 5, further comprising protein dewatering generating protein meal from the protein part.

7. The method of claim 5, further comprising fiber and protein dewatering generating DDG from the protein part.

8. The method of claim 7 further comprising recycling the overflow from the fiber/protein dewatering as part of a backset fluid.

9. The method of claim 5, further comprising recovering the second oil from the oily part from the oil and protein separating.

10. The method of claim 9, wherein the recovering oil is performed without evaporating.

11. The method of claim 9, wherein the recovering oil is performed before evaporating.

12. The method of claim 9, further comprising generating syrup having dry solid higher than 60%.

13. The method of claim 1, wherein the grains comprises corn.

14. The method of claim 1, wherein the first or the second oil comprises corn oil.

* * * * *